(12) United States Patent
Chockalingam et al.

(10) Patent No.: US 11,754,570 B2
(45) Date of Patent: Sep. 12, 2023

(54) METHODS FOR QUANTITATION OF FUNCTIONAL C1 ESTERASE INHIBITOR (FC1-INH)

(71) Applicant: Takeda Pharmaceutical Company Limited, Osaka (JP)

(72) Inventors: Priya Sethu Chockalingam, Arlington, MA (US); Yongquan Lai, Lexington, MA (US); Jiang Wu, Lexington, MA (US); Guodong Zhang, Lexington, MA (US); Zhiwei Zhou, Boston, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 388 days.

(21) Appl. No.: 16/849,601

(22) Filed: Apr. 15, 2020

(65) Prior Publication Data

US 2020/0348311 A1  Nov. 5, 2020

Related U.S. Application Data

(60) Provisional application No. 62/932,011, filed on Nov. 7, 2019, provisional application No. 62/834,461, filed on Apr. 16, 2019.

(51) Int. Cl.
   *G01N 33/68* (2006.01)

(52) U.S. Cl.
   CPC .. *G01N 33/6848* (2013.01); *C12Y 304/21042* (2013.01); *G01N 2333/811* (2013.01); *G01N 2333/96441* (2013.01); *G01N 2800/32* (2013.01); *G01N 2800/52* (2013.01)

(58) Field of Classification Search
   CPC ......... G01N 33/6848; G01N 2333/811; G01N 2800/32; G01N 2800/52; C12Y 304/21042
   See application file for complete search history.

(56) References Cited

U.S. PATENT DOCUMENTS

| 4,849,353 A | 7/1989 | Harpel |
|---|---|---|
| 7,998,679 B2 | 8/2011 | Jacobs et al. |
| 10,690,670 B2 | 6/2020 | Joseph et al. |
| 2007/0231790 A1 | 10/2007 | Su |
| 2009/0064350 A1 | 3/2009 | Dewald |
| 2010/0119512 A1 | 5/2010 | Feener et al. |
| 2011/0140706 A1 | 6/2011 | Groves et al. |
| 2012/0058130 A1 | 3/2012 | Donald |
| 2012/0082676 A1 | 4/2012 | Ghebrehiwet |
| 2012/0201756 A1 | 8/2012 | Sexton |
| 2012/0328517 A1 | 12/2012 | Markland et al. |
| 2014/0335023 A1 | 11/2014 | Sexton et al. |
| 2015/0362492 A1 | 12/2015 | Joseph et al. |
| 2020/0340987 A1 | 10/2020 | Chockalingam et al. |
| 2020/0355700 A1* | 11/2020 | Cozma ............... G01N 33/6893 |
| 2020/0393464 A1 | 12/2020 | Joseph et al. |

FOREIGN PATENT DOCUMENTS

| CN | 1142984 A | 2/1997 |
|---|---|---|
| CN | 1368886 A | 9/2002 |
| CN | 1867679 A | 11/2006 |
| CN | 101023349 A | 8/2007 |
| CN | 101137412 A | 3/2008 |
| CN | 101166762 A | 4/2008 |
| CN | 102216779 A | 10/2011 |
| CN | 102307594 A | 1/2012 |
| EP | 1598428 A1 | 11/2005 |
| JP | S57-94660 A | 6/1982 |
| JP | H3-179264 A | 8/1991 |
| JP | 2003-521914 A | 7/2003 |
| JP | 2003-521914 A5 | 7/2003 |
| JP | 2005-509127 A | 4/2005 |
| WO | WO 01/57079 A2 | 8/2001 |
| WO | WO 02/42775 A2 | 5/2002 |
| WO | WO 2006/091459 A2 | 8/2006 |
| WO | WO 2008/073222 A2 | 6/2008 |
| WO | WO 2008/098720 A1 | 8/2008 |
| WO | WO 2014/113701 A1 | 7/2014 |

OTHER PUBLICATIONS

Feussner (Transfusion 2014 54:2566) (Year: 2014).*
Martin (J. Amer. Soc. Mass Spectrometry 2013, 24:1242). (Year: 2013).*
Kasthuri (Biomarkers 2007 12:287) (Year: 2007).*
Mandle (J. Immunology 1994 152:4680-4685) (Year: 1994).*
Yang (Clinical Chem 2010 56:127) (Year: 2010).*
Attwood, Genomics. The Babel of bioinformatics. Science. Oct. 20, 2000;290(5491):471-3. doi: 10.1126/science.290.5491.471.
Bork, Current management options for hereditary angioedema. Curr Allergy Asthma Rep. Aug. 2012;12(4):273-80. doi: 10.1007/s11882-012-0273-4.
De Smet et al., Clearance of human native, proteinase-complexed, and proteolytically inactivated C1-inhibitor in rats. Blood. Jan. 1, 1993;81(1):56-61.
Govers-Riemslag et al., The plasma kallikrein-kinin system and risk of cardiovascular disease in men. J Thromb Haemost. Sep. 2007;5(9):1896-903.
Kaplan et al., Assessment of Hageman Factor Activation in Human Plasma: Quantification of Activated Hageman Factor-C1 Inactivator Complexes by an Enzyme-Linked Differential Antibody Immunosorbent Assay. Blood. Sep. 1985;66(3):636-641.
Kenniston et al., Inhibition of plasma kallikrein by a highly specific active site blocking antibody. J Biol Chem. Aug. 22, 2014;289(34):23596-608. doi:10.1074/jbc.M114.569061. Epub Jun. 26, 2014.
Lewin et al., Studies of C1 Inactivator-Plasma Kallikrein Complexes in Purified Systems and in Plasma. Journal of Biological Chemistry. May 1983;258(10):6415-6421.
Nuijens et al., Detection of Activation of the Contact System of Coagulation In Vitro and In Vivo: Quantitation of Activated Hageman Factor-C1-Inhibitor and Kallikrein-C1-Inhibitor Complexes by Specific Radioimmunoassays. Thrombosis and Haemostasis. 1987;58(2):778-785.

(Continued)

*Primary Examiner* — Changhwa J Cheu

(57) ABSTRACT

Methods for quantitation of fC1-INH from dried blood spot are provided herein. Such methods may comprise spotting and drying a blood sample on a support member, extracting protein from the dried blood sample and measuring the level of fC1-INH in the extracted proteins.

20 Claims, 7 Drawing Sheets

(56) References Cited

OTHER PUBLICATIONS

Riedl, Hereditary angioedema therapy: kallikrein inhibition and bradykinin receptor antagonism. World Allergy Organ J. Sep. 2010;3(9 Suppl): S34-8. doi:10.1097/WOX.0b013e3181f20dbc.

Schneider et al., Critical role of kallikrein in hereditary angioedema pathogenesis: a clinical trial of ecallantide, a novel kallikrein inhibitor. J Allergy Clin Immunol. Aug. 2007;120(2):416-22. Epub Jun. 7, 2007.

Skolnick et al., From genes to protein structure and function: novel applications of computational approaches in the genomic era. Trends Biotechnol. Jan. 2000;18(1):34-9. doi: 10.1016/s0167-7799(99)01398-0.

Waytes et al., Treatment of hereditary angioedema with a vapor-heated C1 inhibitor concentrate. N Engl J Med. Jun. 20, 1996;334(25):1630-4.

U.S. Appl. No. 16/881,911, filed May 22, 2020, Joseph et al.
U.S. Appl. No. 16/844,463, filed Apr. 9, 2020, Chockalingam et al.
EP 14740167.3, Aug. 1, 2016, Extended European Search Report.
EP 18208603.3, Jan. 8, 2019, Extended European Search Report.
PCT/US2014/012090, Apr. 9, 2014, International Search Report and Written Opinion.
PCT/US2014/012090, Jul. 30, 2015, International Preliminary Report on Patentability.
PCT/US2020/027406, Jul. 31, 2020, International Search Report and Written Opinion.
PCT/US2020/027406, Oct. 21, 2021, International Preliminary Report on Patentability.
PCT/US2020/028205, Jul. 31, 2020, International Search Report and Written Opinion.
PCT/US2020/028205, Oct. 28, 2021, International Preliminary Report on Patentability.

Alsenz et al., Simplified methods for the purification, quantitation, and functional estimation of human complement C1-inhibitor (C1-INH) with a monoclonal anti-C1-INH antibody. J Immunol Methods. Jan. 26, 1987;96(1):107-14. doi: 10.1016/0022-1759(87)90373-5.

Biomarkers Definitions Working Group. Biomarkers and surrogate endpoints: Preferred definitions and conceptual framework. Clin Pharmacol Ther. Mar. 2001;69(3):89-95. doi: 10.1067/mcp.2001.113989.

Caballero et al., Consensus statement on the diagnosis, management, and treatment of angioedema mediated by bradykinin. Part II. Treatment, follow-up, and special situations. J Investig Allergol Clin Immunol. 2011;21(6):422-41.

Chen et al., Enhancement and destruction of antibody function by somatic mutation: unequal occurrence is controlled by V gene combinatorial associations. Embo J. Jun. 15, 1995;14(12):2784-94. doi: 10.1002/j.1460-2075.1995.tb07278.x.

Chockalingam et al., A first of its kind quantitative functional C1-esterase inhibitor lateral flow assay for hereditary angioedema point-of-care diagnostic testing. Int Immunopharmacol. Jun. 1, 2020;83:106526(1-6). doi: 10.1016/j.intimp.2020.106526. Epub Apr. 30, 2020.

Colman PM. Effects of amino acid sequence changes on antibody-antigen interactions. Res Immunol. Jan. 1994;145(1):33-6. doi: 10.1016/s0923-2494(94)80039-1.

D'Angelo et al., Many Routes to an Antibody Heavy-Chain CDR3: Necessary, Yet Insufficient, for Specific Binding. Front Immunol. Mar. 8, 2018;9:395(1-13). doi: 10.3389/fimmu.2018.00395. Supplementary Information, 46 pages.

Kussie et al., A Single Engineered Amino Acid Substitution Changes Antibody Fine Specificity. J Immunol. Jan. 1, 1994;152(1):146-52.

Lai et al., A novel functional C1 inhibitor activity assay in dried blood spot for diagnosis of Hereditary angioedema. Clin Chim Acta. May 2020;504:155-162. doi: 10.1016/j.cca.2020.02.010. Epub Feb. 12, 2020.

Li et al., Comparison of Chromogenic and ELISA Functional C1 Inhibitor Tests in Diagnosing Hereditary Angioedema. J Allergy Clin Immunol Pract. Mar.-Apr. 2015;3(2):200-5. doi: 10.1016/j.jaip.2014.08.002. Epub Oct. 11, 2014.

Mandle et al., Acquired C1 inhibitor deficiency as a result of an autoantibody to the reactive center region of C1 inhibitor. J Immunol. May 1, 1994;152(9):4680-5.

Martin et al., Dried Blood Spot Proteomics: Surface Extraction of Endogenous Proteins Coupled with Automated Sample Preparation and Mass Spectrometry Analysis. J Am Soc Mass Spectrom. Aug. 2013;24(8):1242-9. doi: 10.1007/s13361-013-0658-l. Epub Jun. 1, 2013.

Nuijens et al., Quantification of Plasma Factor XIIa-C1-inhibitor and Kallikrein-C1-inhibitor Complexes in Sepsis. Blood. Dec. 1988;72(6):1841-8.

Prince HE. Biomarkers for diagnosing and monitoring autoimmune diseases. Biomarkers. Nov. 2005;10 Suppl 1:S44-9. doi: 10.1080/13547500500214194.

Rudikoff et al., Single amino acid substitution altering antigen-binding specificity. Proc Natl Acad Sci U S A. Mar. 1982;79(6):1979-83. doi: 10.1073/pnas.79.6.1979.

Varga et al., rhC1INH: a new drug for the treatment of attacks in hereditary angioedema caused by C1-inhibitor deficiency. Expert Rev Clin Immunol. 2011;7(2):143-153. Epub Jan. 10, 2014.

Wagenaar-Bos et al., Functional C1-inhibitor diagnostics in hereditary angioedema: assay evaluation and recommendations. J Immunol Methods. Sep. 30, 2008;338(1-2):14-20. doi: 10.1016/j.jim.2008.06.004. Epub Jul. 23, 2008.

Xie et al., Discovery and development of plasma kallikrein inhibitors for multiple diseases. Eur J Med Chem. Mar. 15, 2020;190:112137(1-14). doi: 10.1016/j.ejmech.2020.112137. Epub Feb. 10, 2020.

\* cited by examiner

1. Buffer Control
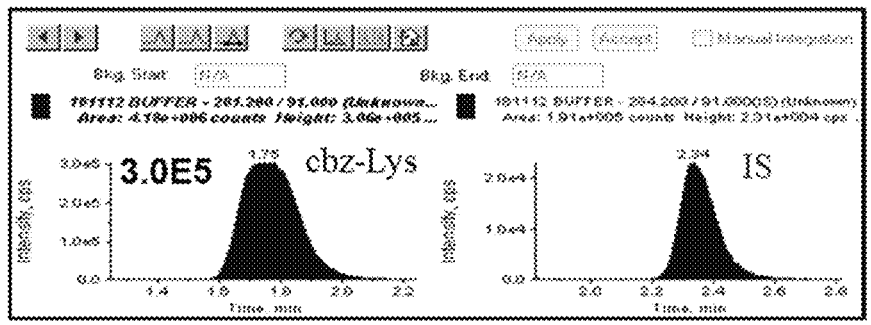
2. Red Blood Cell + BSA Buffer Control
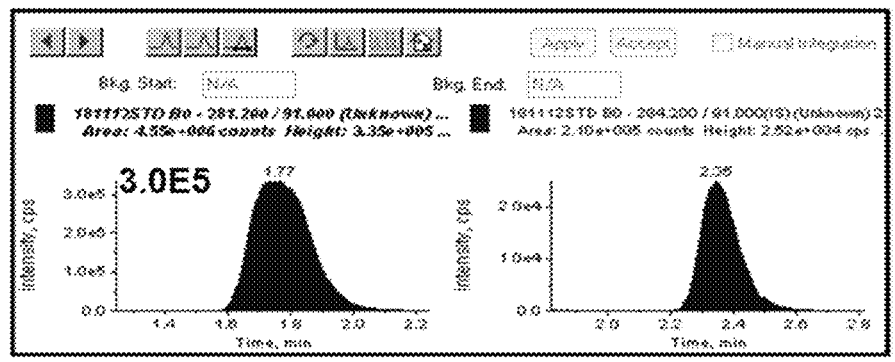
3. Control Whole Blood Sample
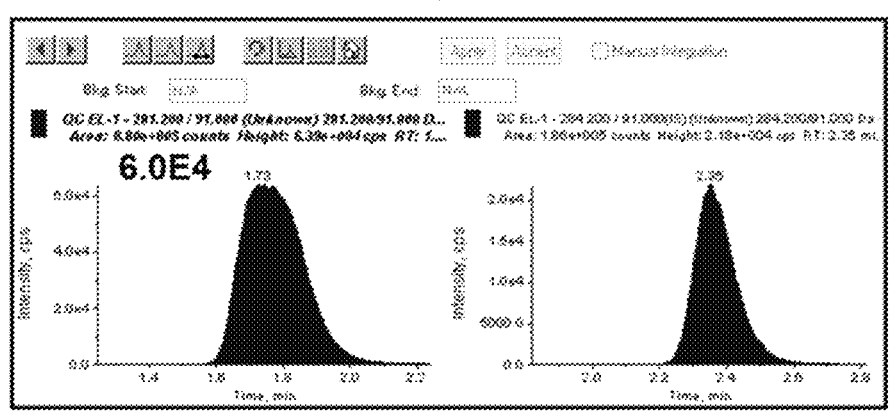
FIGURE 3

FIGURE 6A  Buffer Control
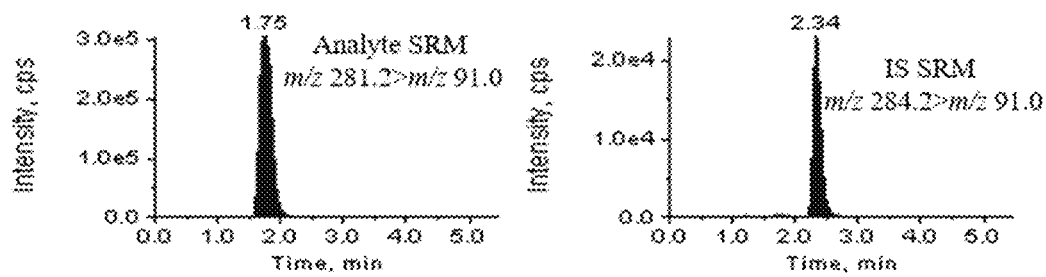
FIGURE 6B  Blank Surrogate Matrix
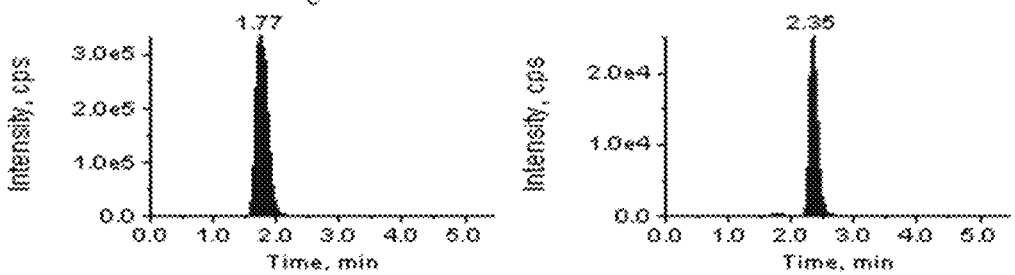
FIGURE 6C  Pooled Healthy Whole Blood
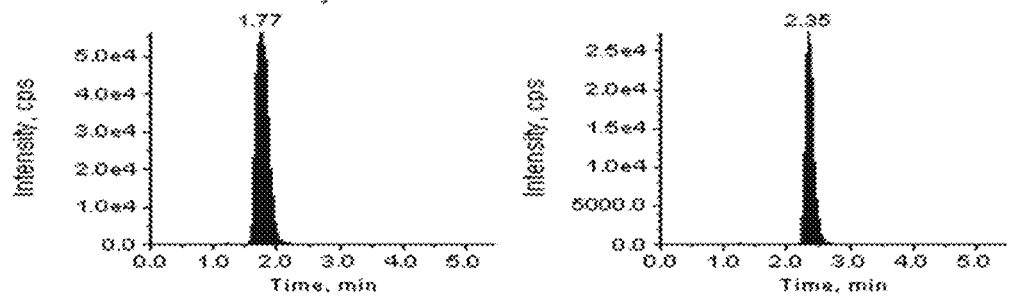
FIGURE 6D  Pooled Healthy Whole Blood Spiked with 500 mU/mL C1INH
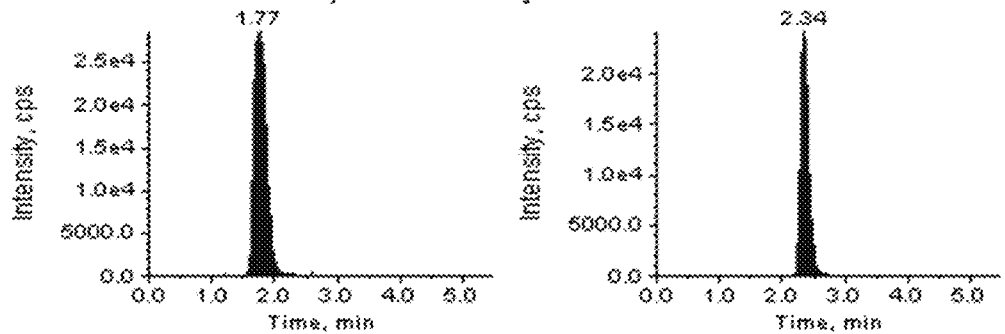

METHODS FOR QUANTITATION OF FUNCTIONAL C1 ESTERASE INHIBITOR (FC1-INH)

RELATED APPLICATIONS

This application claims the benefit under 35 U.S.C. § 119(e) of U.S. provisional application No. 62/834,461, filed on Apr. 16, 2019, and U.S. provisional application No. 62/932,011, filed on Nov. 7, 2019; the entire contents of each is incorporated herein by reference.

BACKGROUND

Hereditary angioedema (HAE) is a rare, autosomal dominant genetic disease caused by an inherited deficiency or dysfunction in the plasma protein C1 esterase inhibitor (briefly C1 inhibitor, C1-INH). HAE is characterized by recurrent episodes of angioedema, which usually involves the face, skin, bowel, and/or airway. The symptoms may be found in other diseases, which make the diagnosis of HAE complex. HAE can primarily be divided in two types. Type I is characterized by low levels of C1-INH protein and accounts for ~85% of the HAE occurrence, whereas type II is characterized by low functional C1-INH (fC1-INH) but normal or elevated C1-INH protein levels and accounts for ~15%. Typical fC1-INH, when measured as Units/ml, in untreated type I and type II patients are 5-30% of the normal levels.

Currently available assays for measuring fC1-INH are plasma-based assays. The frequently used assay is a chromogenic assay, which indirectly measures the inhibition of C1-esterase activity by C1-INH in the test sample using a synthetic C1-esterase specific substrate. Another commonly used assay is an ELISA assay measuring functional binding of C1-INH to Complement protein component C1s. However, sample shipment to and storage in centralized test laboratory is often inconvenient for plasma-based assays.

It is of great interest to develop a simple and user-friendly method that can be run in a central laboratory for measuring fC1-INH in biological samples.

SUMMARY

The present disclosure is based, at least in part, on the development of a simple, sensitive and selective assay, which involves the use of dried blood spots containing functional plasma C1-esterase inhibitor (fC1-INH) for analysis by, e.g., measurement of substrate product derived from the C1-esterase enzymatic reaction (C1s substrate product) via liquid chromatography-mass spectrometry (LC-MS).

Accordingly, one aspect of the present disclosure provides a method for determining the level of fC1-INH in a dried-blood sample, the method comprises: (i) spotting a blood sample from a subject on a support member; (ii) drying the blood sample on the support member to form a dried blood spot; (iii) extracting proteins from the dried blood spot from (ii); and (iv) measuring the level of fC1-INH in the extracted proteins in (iii), if present. Such a measurement may be performed against or compared to a calibration curve. In some examples, the calibration curve may be prepared by serial dilution of the whole blood from normal subjects with C1-INH-free buffers or other suitable components.

In some examples, step (ii) of drying the blood spot may be performed for 3 hours at room temperature. In some examples, the support member is a filter paper. Alternatively or in addition, step (iii) of extracting proteins from the dried blood spot may be performed by incubating the dried blood spot with a bovine serum albumin (BSA)/PBS buffer for at least 3 hours.

In any of the methods disclosed herein, step (iv) of measuring the level of fC1-INH may comprise (a) incubating the extracted proteins with a complement component 1s (C1s) and a C1s substrate to produce a reaction mixture; (b) measuring the level of a C1s substrate product produced in step (a); and (c) determining the level of fC1-INH in the dried blood spot based on the level of the C1s substrate product measured in step (b). In some examples, the C1 substrate products may be measured either by liquid chromatography-mass spectrometry (LC-MS) or liquid chromatography-tandem mass spectrometry (LC-MS/MS).

In some embodiments, step (a) of incubating the extracted proteins with a complement component 1s (C1s) and a C1s substrate may be performed by incubating the extracted proteins with the C1s to produce a reaction mixture, and then incubating the reaction mixture with the C1s substrate to produce a C1s substrate product. In some instances, the level of a C1s substrate product can be measured by liquid chromatography-mass spectrometry. Exemplary C1s substrates include, but are not limited to, $N^\alpha$-Carbobenzyloxy-Lys-ThioBenzyl ester, which produces C1s product $N^\alpha$-Benzyloxycarbonyl-L-lysine (cbz-Lys).

Any of the methods described herein may further comprise obtaining the blood sample (e.g., a whole blood sample) from a subject, e.g., a human subject. In some embodiments, the human subject can be a human patient having or suspected of having a C1-INH deficiency-mediated disorder, such as hereditary angioedema (HAE), for example, type I HAE, or type II HAE.

The methods described herein may further comprise determining whether the subject has HAE. A reduced level of fC1-INH (correlates with an enhanced level of a C1s substrate product) as compared with a control indicates that the subject has a plasma kallikrein (pKal) and/or C1-INH deficiency-mediated disorder, such as HAE as disclosed herein. Any of the methods described herein may further comprise (a) identifying a suitable treatment for the subject based on the level of functional C1-INH; (b) identifying the subject as a candidate for treatment of the disease based on the level of fC1-INH as determined by the method disclosed herein; or both.

Any of the methods described herein may further comprise administering a therapeutic agent to a subject who is identified as being at risk for or having a C1-INH deficiency-mediated disorder by any of the methods disclosed herein. In some embodiments, the therapeutic agent may be a plasma kallikrein (pKal) inhibitor, a bradykinin B2 receptor antagonist, or a C1 esterase inhibitor. Examples include, but are not limited to, ecallantide, lanadelumab, icatibant, or a human plasma-derived C1 esterase inhibitor.

The details of one or more embodiments of the invention are set forth in the description below. Other features or advantages of the present invention will be apparent from the following drawings and detailed description of several embodiments, and also from the appended claims.

BRIEF DESCRIPTION OF DRAWINGS

FIG. 3 includes exemplary ion chromatograms showing cbz-Lys and internal standard derived from neat buffer solution as a control (panel (1)); enzyme reaction of the DBS extracts from surrogate matrix composed of the mixture of red blood cell and BSA solution at optimized volume ratio (panel (2)); and enzyme reaction of the DBS extracts from an authentic whole blood sample from a healthy individual (panel (3)).

FIGS. 6A-6D show exemplary ion chromatograms of representative samples. FIG. 6A shows cbz-Lys and internal standards in a neat buffer solution as a control. FIG. 6B shows cbz-Lys and internal standards in a blank surrogate matrix. FIG. 6C shows cbz-Lys and internal standards in pooled authentic blood. FIG. 6D shows cbz-Lys and internal standards in pooled health blood spiked with 500 mU/mL C1-INH. mU/mL is milliUnits of functional C1-INH levels per milliliter.

DETAILED DESCRIPTION

Figure 1:
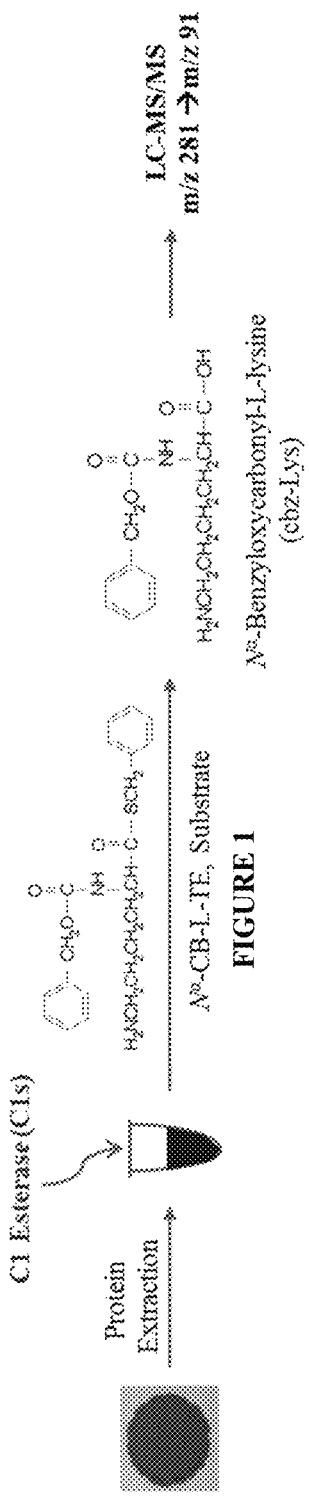
FIG. 1 is a schematic diagram illustrating an exemplary dried blood spot (DBS)-based fC1-INH liquid chromatography-tandem mass spectrometry (LC-MS/MS) assay for analyzing a C1s product (cbz-Lys).

A genetic deficiency in the C1-inhibitor protein (C1-INH) leads to hereditary angioedema (HAE). Patients with HAE suffer from acute attacks of painful edema often precipitated by unknown triggers.

C1 esterase (C1s) inhibitor (C1-INH) is a normal constituent of human plasma and belongs to the group of serine protease inhibitors (serpins) that includes antithrombin III, alpha1-protease inhibitor, alpha2-antiplasmin, and heparin cofactor II. As with the other inhibitors in this group, C1-INH has an important inhibiting potential on several of the major cascade systems of the human body, including the complement system, the intrinsic coagulation (contact) system, the fibrinolytic system, and the coagulation cascade. C1-INH, which is usually activated during the inflammatory process, inactivates its substrate by covalently binding to the reactive site. C1-INH is the only known inhibitor for the subcomponent of the complement component 1 (C1r), C1s, coagulation Factor XIIa, and kallikrein. Additionally, it is the main inhibitor for coagulation Factor XIa in the intrinsic coagulation cascade.

HAE can primarily be divided in two types. Type I is characterized by low levels of C1-INH protein and accounts for ~85% of the HAE occurrence, whereas type II is characterized by low functional C1-INH (fC1-INH) but normal or elevated C1-INH protein levels and accounts for ~15%. Typical fC1-INH, when measured as Units/ml, in untreated type I and type II patients are 5-30% of the normal levels. The accurate and reliable measurement of fC1-INH in samples from patients serves as the basis for HAE diagnosis.

Currently, two types of plasma tests are used to determine the level of fC1-INH. The first assay is a chromogenic assay, which indirectly measures the inhibition of activity of the target protease C1s by C1-INH in the test sample using a synthetic C1s-specific substrate. The second test is an ELISA assay based on functional binding of C1-INH to complement protein component C1s.

Currently, serum or plasma levels of fC1-INH activity and protein expression in conjunction with levels of complement component 4 (C4) are recommended for the diagnosis of HAE type-I/II, with fC1-INH activity the most critical test (see, e.g., Maurer M, et al. *Allergy* (2018)73:1575-96). Conventional methods for measuring fC1-INH activity involve a chromogenic method or a complex-forming immunoassay. The chromogenic method incorporates a synthetic C1s-substrate to measure the inhibitory activity of C1-INH protein in plasma sample where lack of color formation confirms C1-INH-induced inhibition. The complex forming immunoassay method however detects C1-INH-C1s complex formation, without directly measuring C1-INH inhibitory activity (see, e.g., Li H H, et al. *J Allergy Clin Immunol Pract* (2015)3:200-5).

C1-INH and C4 antigen levels are usually measured by turbidimetric assays. These assays would need immediate processing and appropriate storage of blood samples in physician's clinic, and are not standardized, cost-effective, or readily accessible in all geographic regions. To date, the diagnosis rates range from 5-10% in China, Mexico, Japan, Korea to 75-80% in US and Western Europe (unpublished data). It is of great interest to develop simple and standardized methods for measuring fC1-INH in central laboratories.

Dried blood spot (DBS)-based assays have been widely utilized in newborn screening or patient diagnosis of numerous genetic diseases such as lysosomal storage diseases (LSD) (19-23). Results from multiple reports demonstrated enzyme activities can be retained in DBS samples (2, 24). Compared to conventional plasma or serum assays, DBS provides unique advantages. First, DBS sampling, for example using a finger prick, is less-invasive and does not require large volumes of blood and any laboratory equipment. Secondly, DBS samples can be transported and stored long term at ambient temperature without significantly losing enzyme activity or genetic information. These advantages warrant that the DBS samples can be prepared in a physician's office and tested in centralized laboratories.

The present disclosure describes assays for measuring functional C1 inhibitor (fC1-INH) levels in a dried-blood spot (DBS). This DBS-based test offers several advantages over the plasma-based chromogenic or ELISA assays, for example, small blood volume, extended analyte stability once dried on filter paper, easy sample transportation and storage, and/or allows the patient samples to be tested in centralized laboratories.

I. Method for Detecting the Level of Functional Plasma Esterase C1 Inhibitor (fC1-INH)

The present disclosure relates to methods of determining fC1-INH levels by a robust liquid chromatography-tandem mass spectrometry (LC-MS/MS) using a dried-blood spot (DBS) prepared from a patient's whole blood sample(s). Such methods can be utilized for the diagnosis of C1-INH-deficiency-mediated disorders, such as HAE. The methods may involve preparation of DBS samples, extraction of proteins from DBS samples, incubation of the protein extract with complement component 1s (C1s), and reaction with a C1s substrate to generate a C1s substrate product, which can be measured by, e.g., liquid chromatography-tandem mass spectrometry (LC-MS/MS).

(i) Sample Preparation

Any sample that may or may not contain C1-INH (e.g., fC1-INH, non-functional C1-INH, or both) may be analyzed by the methods described herein. As used herein, a "sample" refers to a composition that may comprise an analyte of interest (fC1-INH in the present case). A sample may comprise tissue, blood, plasma, or serum, from a subject. The term "sample" may encompass both an initial unprocessed sample taken from a subject as well as subsequently processed, e.g., partially purified or preserved forms, for example, via immunoprecipitation. Exemplary samples include blood, plasma, serum, tears, or mucus. In other examples, a sample may be a composition from an in vitro assay.

In some embodiments, the sample is a body fluid sample, such as a serum or plasma sample. In some embodiments, the sample is a biological sample obtained from a subject in need of the analysis. A "patient," "subject," or "host" (these terms are used interchangeably) may refer to either a human or non-human animal. In some instances, the subject is a human patient, who may have, be suspected of having, or be at risk for a disease associated with the contact system. For example, the human patient may have a prior occurrence of HAE or may be at risk for HAE. Such a human patient may be treated previously or may be in the course of treatment with a drug that targets a component of the contact system (e.g., C1s, plasma kallikrein).

The biological sample may be a bodily fluid sample, e.g., a blood sample. In some examples, the blood sample is whole blood sample. Whole blood comprises red blood cells, white blood cells, platelets, and blood plasma. In some embodiments, the blood sample may be collected from blood vessels (e.g., capillaries, veins, and arteries). The whole blood sample for use in the methods described herein may be collected and processed using any method known in the art. In some embodiments, the sample is obtained by a finger prick (fingerstick). In some embodiments, the sample may be collected using an evacuated blood collection tube.

Samples of the present disclosure may be of any volume sufficient for performance of at least one fC1-INH measurement assay as described herein. In some embodiments, a sample obtained from a subject is between 25 µL-10 mL. In some embodiments, a sample or an aliquot thereof for use in the methods described herein is between 100 µL-2 mL. In some embodiments, a sample is between 50 µL-100 µL. In some embodiments, a sample is between 50 µL-1 mL. In some embodiments, a sample is 50 µL, 100 µL, 200 µL, 300 µL, 400 µL, 500 µL, 600 µL, 700 µL, 800 µL, 900 µL, 1 mL, 1.1 mL, 1.2 mL, 1.3 mL, 1.4 mL, 1.5 mL, 1.6 mL, 1.7 mL, 1.8 mL, 1.9 mL, 2.0 mL, 2.5 mL, 3.0 mL, 3.5 mL, 4.5 mL, 5.0 mL, 5.5 mL, 6.0 mL, 6.5 mL, 7.0 mL, 7.5 mL, 8.0 mL, 8.5 mL, 9.0 mL, 9.5 mL, or 10.0 mL. In some embodiments, the sample is 60 µL.

Any of the samples disclosed herein, for example, a whole blood sample, may be collected and an aliquot of the sample may be removed and spotted on a support member. In some embodiments, the support member containing the sample or an aliquot of the sample is maintained under suitable conditions (e.g., room temperature) for a suitable period (e.g., at least 1 hour, at least 2 hours, at least 3 hours, at least 4 hours, or longer) to allow for formation of a dried spot of the sample on the support member.

The support member may be a membrane, a film, a filter paper, or a dried-blood spot card. In some embodiments, the support member may comprise one or more sample collection areas and, optionally, a wrap-around cover. The support member may fit into a sealable container, for example, a Ziploc® bag, to facilitate sample transportation. In some embodiments, the support member can be foldable. Any of the support members described herein may further comprise one or more areas for recording additional information of the sample (e.g., demographic information of the subject).

The sample (or an aliquot thereof) may be allowed to dry on the support member within a suitable period of time under suitable conditions. In some embodiments, the sample is allowed to dry for about 1-6 hours, for example, 1 hour, 2 hours, 3 hours, 4 hours, 5 hours, or 6 hours. In some embodiments, the sample is allowed to dry for about 1-2 hours, 1-3 hours, 1-4 hours, 1-5 hours, 2-3 hours, 2-4 hours, 2-5 hours, 2-6 hours, 3-4 hours, 3-5 hours, 3-6 hours, 4-5 hours, 4-6 hours, or 5-6 hours.

In some embodiments, the sample is allowed to dry at a suitable temperature, for example, at a temperature between 10° C.-40° C., or higher. In some embodiments, the sample is allowed to dry at a temperature of 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., or higher. It is known to those skilled in the art that the drying process may be performed under a relatively higher temperature for a shorter period, or alternatively, under a relatively lower temperature for a longer period. In some examples, the sample can be allowed to dry for at least 3 hours at room temperature (about 25° C.).

(ii) Protein Extraction

The dried spot sample, e.g., dried blood sample, prepared as described herein may be processed to extract the biological materials contained in the sample, for example, proteins. In some embodiments, the dried spot samples, such as DBS samples, can be processed for protein extraction. Protein extraction, as used herein, refers to extracting protein, or a certain portion of the proteins, contained in the dried sample into a suitable buffer (e.g., in which the target proteins are soluble). In some instances, the dried spot samples, such as DBS samples, present on the sample collection areas of the support member can be isolated from the rest of the support member by conventional methods (e.g., using a puncher). The isolated biological material samples, such as protein samples, can be transferred to a suitable container for further protein extraction. Non-limiting examples of suitable containers can be tubes, dishes, vials, multi-well plates. In some examples, the suitable container can be a 96 well plate. One or more dried spot samples such as DBS samples can be simultaneously processed.

Any suitable buffer can be used in the methods described herein. Preferably the buffers are compatible with biological materials to be extracted (e.g., capable of dissolving proteins and preferably retaining protein function). Non-limiting examples of suitable buffers include phosphate-buffered saline (PBS), Dulbecco's phosphate-buffered saline (DPBS), or Hanks' Balanced Salt Solution (HBSS). In some examples, the buffer can be PBS. In some embodiments, the buffer may contain one or more components to promote stability and/or prevent degradation of the biological materials to be extracted.

In some embodiments, the buffer for use in the extraction step may comprise one or more agents that would facilitate protein extraction (e.g., bovine serum albumin) at a suitable concentration (e.g., 0.5%). In some embodiments, the support member or a portion thereof containing the dried spot sample (e.g., a DBS samples) can be incubated in the buffer under suitable conditions allowing for complete extraction of the biological materials of interest in the sample (e.g., fC1-INH). In some embodiments, the dried spot sample-containing support member can be incubated in the buffer under a suitable temperature, for example, 25-37° C. (e.g., 37° C.), for a suitable period, for example, 2-5 hours (e.g., 3 hours), to allow for sufficient extraction of the biological materials of interest (e.g., proteins including fC1-INH) such that the level of fC1-INH may be measured.

In some embodiments, the buffer/sample mixture may be centrifuged at a suitable speed, for example, 800-2000 rpm (e.g., 1250 rpm), to facilitate extraction of the biological materials into a solution. Selection of specific extraction conditions, including temperature, extraction time period, usage of buffer, with or without centrifugation, the speed of the centrifugation, etc., may depend, for example, on the type of biological materials to be extracted and the support member used for formation of the dried spot sample. Such information would have been within the knowledge of those skilled in the art.

(iii) Measurement of fC1-INH

A solution containing fC1-INH prepared as disclosed above can be analyzed to determine the level of fC1-INH in the solution. In some instances, the level of fC1-INH is measured by determining the activity of fC1-INH, e.g., by conventional approaches or methods disclosed herein.

Levels of fC1-INH may be measured using a suitable approach as known in the art or as described herein. In some embodiments, the level of fC1-INH is measured by a chromogenic assay using a chromogenic substrate that can be cleaved by C1s. In some embodiments, an immune assay is used for assessing levels of a C1s product of interest, as described herein. Examples of immune assays include, without limitation, Western blots, enzyme linked immunosorbent assays (ELISAs) (e.g., sandwich ELISAs), radioimmunoassays, electrochemiluminescence-based detection assays, and related techniques. Assays, e.g., Western blot assays, may further involve use of a quantitative imaging system, e.g., LICOR imaging technology, which is commercially available (see, e.g., the Odyssey® CLx infrared imaging system from LI-COR Biosciences). In some embodiments, an electrochemiluminescence detection assay or an assay relying on a combination of electrochemiluminescence and patterned array technology is used (e.g., an ECL or MULTI-ARRAY technology assay from Meso Scale Discovery (MSD)).

As used herein, the terms "measuring" or "measurement," or alternatively "detecting" or "detection," mean assessing the presence, absence, quantity, or amount (which can be an effective amount) of a substance within a sample, including the derivation of qualitative or quantitative concentration levels of such substances, or otherwise evaluating the values or categorization of a subject.

In some embodiments, the fC1-INH-containing sample extracted from any of the dried spot samples (e.g., DBS samples) disclosed herein may be incubated with C1s protease and a C1s substrate. The C1s protease can act on the C1s substrate to convert the C1s substrate to a C1s substrate product, which can then be analyzed to determine the presence and/or level of the C1s substrate product. Alternatively, the C1s substrate may be analyzed to determine the presence and/or level of C1s substrate remaining following incubation with the C1s protease and the fC1-INH-containing sample. Once the C1s protease is inhibited by fC1-INH, production of the C1s substrate product would be decreased or eliminated. A "C1s substrate product," as used herein, refers to a cleaved product generated from the protease reaction of C1s on a C1s substrate. In some embodiments, the amount of C1s substrate and/or C1s substrate product may be used as an indirect measure of activity of C1s protease and/or fC1-INH.

In some embodiments, the fC1-INH-containing sample extracted from any of the dried spot samples (e.g., DBS samples) disclosed herein may be incubated first with C1s protease under suitable conditions for a suitable period. A C1s substrate may then be added to the mixture, which may be further incubated under suitable conditions for a suitable period to allow for generation of the C1s substrate product. In some embodiments, the incubation may be performed in the dark. In some examples, the method may comprise a step of quenching the C1s protease reaction, which may increase the accuracy of the analysis. In some embodiments, quenching the C1s protease reaction may be achieved by diluting (e.g., 1:5-1:20) the C1s reaction mixture in a quenching solution. A "quenching solution," as used herein, refers to a solution for stopping the enzymatic reaction (e.g., a C1s protease reaction), as described herein. In some embodiments, a quenching solution may comprise an agent capable of denaturing or inactivating the enzyme. Non-limiting denaturing agents include alcohols, detergents, strong acids, strong bases, chelating agents, etc. In some embodiments, the quenching solution may contain a detergent (e.g., SDS) and/or an alcohol (e.g., methanol).

The C1s substrate for use in the methods disclosed herein may be any substrate that can be cleaved by C1s protease to generate a detectable C1s substrate product. Non-limiting examples of C1s substrates include Nα-Carbobenzyloxy-Lys-ThioBenzyl ester, which generates Nα-Benzyloxycarbonyl-L-lysine (cbz-Lys) upon C1s protease cleavage; and C4, which generates C4a and C4b.

In some embodiments, after the enzymatic reaction is quenched, the sample can be further diluted for subsequent liquid chromatography-tandem mass spectrometry (LC-MS/MS) analysis. In some embodiments, the sample may be diluted 200-fold in a suitable solution (e.g., 80% MeOH in water (v/v)).

The C1s substrate product thus generated can be analyzed by conventional methods to determine its presence and/or level. In some embodiments, the C1s substrate product can be analyzed by a liquid chromatography-mass spectrometry (LC-MS) approach, which is an analytical technique that combines the physical separation capabilities of liquid chromatography with the mass analysis capabilities of mass spectrometry (MS). The LC-MS/MS assay can be performed using routine methods.

In some instances, a mass spectrometer for use in analyzing a C1s substrate product may be operated under the selective reaction monitoring (SRM) mode. SRM mode is a highly sensitive and selective method for tandem mass spectrometry in which an ion of a particular mass is selected in the first stage of a tandem mass spectrometer and an ion product of a fragmentation reaction of the precursor ion is selected in the second mass spectrometer stage for detection. SRM mode may be used for targeted quantitation by mass spectrometry. Following ionization, for example, using an electrospray source, a precursor is first isolated to obtain a substantial ion population of mostly the intended species (e.g., parent ion). This population is then fragmented to yield product ions whose signal abundances are indicative of the abundance of the product of interest in the sample. In some embodiments, the cbz-Lys parent ion can be at m/z 281 and the cbz-Lys product ion chosen for detection can be at m/z 91. As described in the Examples, a suitable instrument, such as an ABSciex 5500 or 6500 QTrap mass spectrometer, may be used and differences between various samples may be assessed after method optimization. Individual whole blood samples may be prepared for LC-MS/MS analysis, as described herein.

The level (e.g., concentration) of C1s substrate product (e.g., represented by AUC), and thus the fC1-INH concentration can be determined via conventional methods. A calibration or standard curve (e.g., a four-parameter logistic calibration curve) can be generated by plotting the concentrations of fC1-INH against the peak area ratios of the analyte (e.g., cbz-Lys) over the internal standard (e.g., concentrations of Nε-Benzyloxycarbonyl-L-lysine-2, 6, 6-d3). The calibration curve can be fitted into an equation, for example:

$$y = D + \frac{A - D}{1 + \left(\frac{x}{C}\right)^2} \quad \text{(Equation 1)}$$

where y refers to the peak area ratio; x refers to the sample concentration; and A, B, C and D are curve fitting parameters.

In some embodiments, the LC-MS/MS methods may be validated for accuracy and reproducibility by analyzing the calibration standard prepared using the methods described herein. In some embodiments, the level of (e.g., concentration) of fC1-INH in a sample can be calculated by the equation (e.g., Equation 1). These results indicate that the level of fC1-INH, represented and calculated by the level of C1s substrate product in the sample, prepared by the method described herein, is a reliable biomarker for HAE diagnosis.

In some instances, a calibration curve can be constructed with peak area ratios of an analyte of interest (a C1s signature product) over an internal standard. As used herein, an "internal standard" refers to a chemical substance that is added in a constant amount to testing samples, quality control (QC) samples, the blank, and calibration standards to correct for the loss of analyte during sample preparation and thus to enhance accuracy of the analyte analysis. In some embodiments, the internal standard is Nε-Benzyloxycarbonyl-L-lysine-2,6,6-d3 or another stable isotope-labeled C1s substrate product. In some embodiments, the calibration curve may be used for quantitative analysis.

In addition, a serial of calibration standards can be prepared and subjected to LC-MS/MS analysis with the samples as calibrators of the assay and for quality control purposes. A calibration standard, as used herein, refers to a whole blood or solution that contains a known amount of the analyte or material of interest (e.g., fC1-INH in the present disclosure). Calibration standards may be used for testing materials of known concentration in the same manner as the samples to assure the test system is accurately measuring samples throughout the reportable range. Calibration standards may be prepared by adding various known amounts of the material of interest (e.g., fC1-INH) into a solution that does not initially contain or is depleted of the material of interest. In some examples, the material of interest (e.g., fC1-INH) may be added into biological samples similar to the testing samples (e.g., whole blood sample) to mimic the testing samples (e.g., surrogate matrix). In one example, the calibration standard can be prepared by mixing fC1-INH (e.g., purified fC1-INH) with fC1-INH depleted surrogate blood. The fC1-INH depleted surrogate blood, as used herein, can be prepared by (i) obtaining and/or pooling fresh whole blood from a suitable population, ideally the same species as the subject (e.g., healthy individuals, males and/or females) by a suitable method (e.g., evacuate blood collection tubes); (ii) depleting endogenous material of interest (e.g., fC1-INH) in the blood sample by removing supernatant plasma using a suitable method (e.g., centrifugation at 800 rpm at room temperature for 10 min); (iii) mixing a suitable volume (e.g., equal volume) of the pooled remaining red blood cells with a suitable buffer (e.g., ~4.3% BSA in PBS). Calibration standards and quality controls (QCs) for the material of interest (e.g., fC1-INH) can be prepared by spiking various known concentration of a solution containing the material of interest (e.g., fC1-INH) into the fC1-INH depleted surrogate blood, as described herein. The calibration standard can be subjected to the method of generating the C1s substrate product, as described herein, prior to LC-MS/MS analysis.

In one specific example, the methods described herein may comprise: (1) procedures for the preparation of a DBS card from whole blood samples; (2) extraction of C1-INH protein from the DBS card; (3) incubation of the extracted proteins with complement component C1s; (4) an enzyme reaction with C1s substrate, $N^{\alpha}$-Carbobenzyloxy-Lys-Thio-Benzyl ester, to generate enzyme product, $N^{\alpha}$-Benzyloxycarbonyl-L-lysine (cbz-Lys); and (5) subsequently measurement of cbz-Lys by LC-MS assay using $N^{\varepsilon}$-Benzyloxycarbonyl-L-lysine-2,6,6-d3 as an internal standard for quantitation.

II. Application of the Dried Spot Assay Methods

The assay methods for measuring fC1-INH in samples described herein may be used for clinical or non-clinical purposes.

(i) Disease Diagnosis and Prognosis

Diagnosis of C1-INH deficiency-mediated disorder, such as hereditary angioedema (HAE), may be based on the level of fC1-INH in a sample obtained from a candidate subject.

The assay methods, and kits described herein can be applied for evaluation of a disease, e.g., diagnosis or prognosis of a disease. Evaluation may include identifying a subject as being at risk for or having a disease as described herein, e.g., a C1-INH deficiency-mediated disorder such as HAE (e.g., Type I HAE or Type II HAE). Evaluation may also include monitoring treatment of a disease, such as evaluating the effectiveness of a treatment for a C1-INH deficiency-mediated disorder, such as HAE. Further, evaluation may include identifying a disease that can be treated by a pKal inhibitor, such as a C1s inhibitor (e.g., a C1s inhibitor derived from human plasma) or plasma kallikrein inhibitor.

A. Diagnosis

In some embodiments, the assay, methods, and kits described herein are used to determine the level of fC1-INH in a biological sample (e.g., a whole blood sample) collected from a candidate subject (e.g., a human patient suspected of having a C1-INH deficiency-mediated disorder (e.g., HAE)). The level of fC1-INH can be determined based on the level of a C1s substrate product generated by the method described herein (e.g., by 4-parameter logistic calibration curve). Such an fC1-INH level can be compared to a predetermined reference value or reference ratio to determine whether the subject has or is at risk for the C1-INH deficiency-mediated disorder, e.g., HAE. For example, if the fC1-INH in sample of a candidate subject is at or lower than a reference value, the subject can be identified as having or at risk for a C1-INH deficiency-mediated disorder, such as HAE.

The reference sample can be a control level of the fC1-INH as described herein. In some embodiments, the control level represents the amount of fC1-INH in a control sample (e.g., whole blood sample) obtained from a healthy subject or a population of healthy subjects, which preferably are of the same species and age as the candidate subject. As used herein, a healthy subject is a subject that is apparently free of the target disease (e.g., a C1-INH deficiency-mediated disorder, such as HAE) at the time the level fC1-INH is measured or has no history of the disease.

Alternatively, the reference value may be a predetermined value. Such a predetermined signature fC1-INH can represent the value of fC1-INH as described herein in a population of subjects that do not have or are not at risk for the target disease.

The predetermined value can take a variety of forms. For example, it can be single cut-off value, such as a median or mean. In some embodiments, the predetermined level can be established based upon comparative groups, such as where one defined group is known to have a target disease and another defined group is known to not have the target disease. Alternatively, the predetermined level may be a range, for example, a fC1-INH range in a control population within a predetermined percentile.

The control value as described herein may be determined by routine technology. In some examples, the control value may be obtained by performing a conventional method (e.g., the same assay for obtaining the level of fC1-INH as described herein) on a control sample as also described herein. In other examples, levels of the fC1-INH can be obtained from members of a control population and the results can be analyzed by, e.g., a computational program, to obtain the control level (a predetermined level) that represents the level of fC1-INH in the control population.

By comparing the concentration of fC1-INH described herein in a sample obtained from a candidate subject to the reference ratio as described herein, it can be determined as to whether the candidate subject has or is at risk for the C1-INH deficiency-mediated disease (e.g., HAE). For example, if the value of the fC1-INH in a sample of the candidate subject deviates from the reference value or ratio (e.g., decreased as compared to the reference value), the candidate subject may be identified as having or being at risk for the disease. When the reference value represents the value range of the fC1-INH as described herein in a population of subjects that have the target disease, the value of the fC1-INH in a sample of a candidate falling in the range indicates that the candidate subject has or is at risk for the target disease.

As used herein, "a decreased value below a reference value" means that the level of fC1-INH is lower than a reference value, such as a pre-determined threshold of fC1-INH in a control sample. Control levels are described in detail herein. A decreased value of fC1-INH includes a value that is, for example, 1%, 5%, 10%, 20%, 30%, 40%, 50%, 60%, 70%, 80%, 90%, 100%, 150%, 200%, 300%, 400%, 500% or more lower than a reference value of the control samples.

In some embodiments, the candidate subject is a human patient having one or more symptoms of a C1-INH deficiency-mediated disorder, e.g., such as HAE. For example, the subject may have edema, swelling wherein said swelling is completely or predominantly peripheral; hives; redness, pain, and swelling in the absence of evidence of infection; non-histamine-mediated edema, recurrent attacks of swelling, or a combination thereof. In other embodiments, the subject has no symptoms of a C1-INH deficiency-mediated disorder at the time the sample is collected, has no history of a symptom of a C1-INH deficiency-mediated disorder, or no history of a C1-INH deficiency-mediated disorder such as HAE. In yet other embodiments, the subject is resistant to an anti-histamine therapy, a corticosteroid therapy, or both.

B. Identifying Suitable Treatment

In some embodiments, the assay methods and kits described herein may also be used to identify a suitable treatment for a subject having or at risk of having a C1-INH deficiency-mediated disorder (e.g., Type I HAE or Type II HAE). For example, the level of fC1-INH of a subject may be measured using any of the methods as described herein and compared to a predetermined value of fC1-INH. If the fC1-INH value of the subject is at or lower than the predetermined value, the subject may be treated by treatments based on the predetermined value of fC1-INH (e.g., recombinant C1-INH therapeutic agent or other therapeutic agent as described herein). In some examples, the subject may be a candidate for treatment of the disease based on the level of fC1-INH.

In some embodiments, the methods described herein further comprise administering a therapeutic agent to a subject having or at risk for having a C1-INH deficiency-mediated disorder (e.g., HAE). Non-limiting examples of therapeutic agents include a plasma kallikrein (pKal) inhibitor (e.g., ecallantide, lanadelumab), a bradykinin B2 receptor antagonist (e.g., icatibant), and a C1s inhibitor (e.g., a human plasma-derived C1s inhibitor).

(ii) Non-Clinical Application

Further, the assay methods described herein may have non-clinical applications, for example, for research purposes and/or pre-clinical drug development purposes. Although many diseases associated with C1-INH deficiency have been identified, it is possible that other diseases are mediated by similar mechanisms or involve similar components. In some embodiments, the methods described herein may be used to identify a disease as being associated with C1-INH deficiency. In some embodiments, the methods described herein may be used to study mechanisms (e.g., the discovery of novel biological pathways or processes involved in disease development) or progression of a disease.

In some embodiments, the level of fC1-INH determined by the assay methods as described herein may be used in the development of new therapeutics for a disease associated with C1-INH deficiency. For example, the level of fC1-INH as described herein may be measured in samples obtained from a subject having been administered a new therapy (e.g., gene therapy), or in samples obtained from in vitro assays. In some embodiments, the fC1-INH level may indicate the activity of the new therapeutic in in vitro assays or the efficacy of the new therapeutic in clinical trial settings.

III. Kits for Performing Dried Spot Assay Methods

The present disclosure also provides kits for use in measuring the level of fC1-INH as described herein. Such a kit may comprise materials for collecting and preparing a sample, extracting proteins from a sample, components for measuring fC1-INH in a sample, and/or instructions for assaying fC1-INH levels in a sample.

In some embodiments, the kit comprises a support member, such as a membrane, filter paper, or dried blood spot card. Selection of an appropriate support member for the method will depend on various factors such as the number of samples to be assessed and method of extracting proteins from the sample.

In some embodiments, the support member is a multi-well plate, such as an ELISA plate. In some embodiments, the immunoassays described herein can be carried out on high throughput platforms. In some embodiments, multi-well plates, e.g., 24-, 48-, 96-, 384- or greater well plates, may be used for high throughput immunoassays. Individual immunoassays can be carried out in each well in parallel. Therefore, it is generally desirable to use a plate reader to measure multiple wells in parallel to increase assay throughput. In some embodiments, plate readers that are capable of imaging multi-wells (e.g., 4, 16, 24, 48, 96, 384, or greater wells) in parallel can be used for this platform.

The kit can also comprise one or more buffers as described herein but not limited to quenching buffers, denaturing buffers, and protein extraction buffers. Examples of buffers include, without limitation, PBS, DPBS, HBSS, HEPES, Tris, Tris-HCl, sodium phosphate, potassium phosphate, and potassium chloride.

In some embodiments, the kit can comprise instructions for use in accordance with any of the methods described herein. The included instructions can comprise a description of how to use the components contained in the kit for measuring the level of fC1-INH in a biological sample collected from a subject, such as a human patient.

The instructions relating to the use of the kit generally include information as to the amount of each component and suitable conditions for performing the methods described herein. The components in the kits may be in unit doses, bulk packages (e.g., multi-dose packages), or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the kit is used for evaluating the level of fC1-INH in one or more samples. Instructions may be provided for practicing any of the methods described herein. In some embodiments, the kit may include sealable containers (e.g., Ziploc® bag) for transport of a dried sample prior to analysis.

The kits of this present disclosure are in suitable packaging. Suitable packaging includes, but is not limited to, vials, bottles, jars, flexible packaging (e.g., sealed Mylar or plastic bags), and the like.

Kits may optionally provide additional components such as interpretive information, such as a control and/or standard or reference sample, for example to generate a calibration curve. Normally, the kit comprises a container and a label or package insert(s) on or associated with the container. In some embodiments, the present disclosure provides articles of manufacture comprising contents of the kits described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: DBS-Based LC-MS/NIS fC1-INH Assay

This Example describes a dried blood spot (DBS)-based LC-MS/MS analysis for measuring functional C1-inhibitor (fC1-INH) in blood samples. FIG. 1 illustrates an exemplary scheme of this assay.

The method aims to determine fC1-INH levels in human whole blood samples. The method involves preparation of calibration standards, quality controls (QCs), and DBS samples, extraction of proteins from DBS samples, incubation of the protein extract with complement component 1s (C1s), reaction with C1s substrate, Nα-Carbobenzyloxy-Lys-ThioBenzyl ester to generate Nα-Benzyloxycarbonyl-L-lysine (cbz-Lys), and subsequent measurement of the cbz-Lys using liquid chromatography-tandem mass spectrometry (LC-MS/MS). The AB Sciex QTrap 6500 mass spectrometer was operated in the Selected Reaction Monitoring (SRM) mode under optimized conditions for the detection of cbz-Lys and internal standard (Nε-Benzyloxycarbonyl-L-lysine-2,6,6-d3) in the positive ion mode.

Experimental Procedures:

(i) Preparation of Calibration Standards and Quality Controls (QCs)

Calibrators and quality controls (QCs) were prepared from the surrogate blood that was depleted of the C1-INH protein. Briefly, fresh whole blood from healthy individuals (males and females) were pooled and centrifuged at 1200×g and room temperature for 10 min. The supernatant plasma was discarded and the resulting red blood cells were washed once with phosphate-buffered saline (PBS) solution. The C1-INH-free surrogate blood was prepared by mixing equal volume of pooled red blood cells and 4.3% bovine serum albumin (BSA) in PBS. To prepare calibration standards and QCs, different concentrations of the C1-INH solution were spiked into the surrogate blood.

(ii) Preparation of DBS Samples

After whole blood specimen was collected, a maximum of 60 μL aliquot was deposited on the filter paper spot of a DBS card (903 Protein Saver Card, Whatman). The DBS cards were bent so that the backside was not in contact with any surface to prevent loss of blood that soaked through the filter paper. The cards were allowed to dry for at least 3 hours (h) and stored at room temperature.

For the preparation of calibrators, QCs, and testing samples, a 3.0 mm hole was punched using a DBS Puncher (GE Health Care Life Science Whatman) and DBS samples were transferred to a vial of 500 μL 96-well plate (Eppendorf Protein Lobind). The DBS samples were extracted by incubation at 37° C. for 3 hours with 100 μL of 0.5% BSA in PBS buffer in an incubator operated at 1250 rpm. An aliquot (20 μL) of the extracted samples was transferred to another 96-well plate and was allowed to mix with 50 μL of 0.5 μg/mL C1s solution freshly prepared in 0.5% BSA in PBS. After incubation at 800 rpm and 37° C. for 1.5 hours, a 105 μL mixture of substrate solution (Nα-Carbobenzyloxy-Lys-ThioBenzyl ester) and internal standard (Nε-Benzyloxycarbonyl-L-lysine-2,6,6-d3) was added and enzyme reaction was allowed to proceed by incubation in dark at room temperature for 40 min. The reaction was quenched by transferring 50 μL of reaction solution to 450 μL of 0.1% SDS in MeOH/Water (80/20, V/V). The above sample was further diluted 200-folds with MeOH/Water (80/20, V/V) prior to LC-MS/MS analysis.

(iii) LC-MS/MS Analysis

The separation of unreacted substrate, substrate product (analyte, cbz-Lys), and internal standard was achieved on a Waters Acquity UPLC using a reversed-phase column (Waters Xbridge Protein BEH C4, 3.5 μm, 2.1×50 mm) set at 30° C. The mobile phase A was 0.1% formic acid in water and mobile phase B was acetonitrile. The flow rate was 0.3 ml/min and the mobile phase gradient was composed of gradient steps between the following time points (time, % B): 0 min, 4%; 0.5 min, 4%; 3.5 min, 12%; 3.6 min, 70%; 4.6 min, 70%; 4.7 min, 4%; 5.5 min, 4%. Auto-sampler temperature was set at 4° C., and 3 μL of sample was injected in partial-loop LC injection mode. The analyte and internal standard signals were acquired on an AB Sciex QTrap 6500 mass spectrometer operated in the Selected Reaction Monitoring (SRM) mode using positive ions formed by electrospray ionization, under optimized settings for the detection of cbz-Lys and internal standard (Nε-Benzyloxycarbonyl-L-lysine-2,6,6-d3).

The optimized MS parameter settings were as follows: Curtain Gas, 20; Collision Gas, medium; IonSpray Voltage, 4000; Temperature, 550; Ion Source Gas 1, 50; Ion Gas Source 2, 50; Declustering Potential, 120; Entrance Potential, 10.0; Collision Energy, 26.0; Collision Cell Exit Potential, 12.0. The analyte and internal standard were monitored with SRM ions of m/z 281.2 to m/z 91.0 and m/z 284.2 to m/z 91.0, respectively.

(iv) Data Analysis

Peak areas of the analyte and internal standard were determined by Analyst software. A 4-parameter logistic calibration curve was constructed with peak area ratios of analyte over internal standard and the concentration of spiked fC1-INH in standards using SoftMax Pro 7.0. The fC1-INH levels in samples were calculated based on following equation.

$$y = D + \frac{A - D}{1 + \left(\frac{x}{C}\right)^2} \quad \text{(Equation 1)}$$

Where y is the peak area ratio; x is sample concentration; A, B, C and D are curve fitting parameters. In addition, the accuracy and relative standard deviation (RSD) were calculated using Excel.

Results

Figure 2:
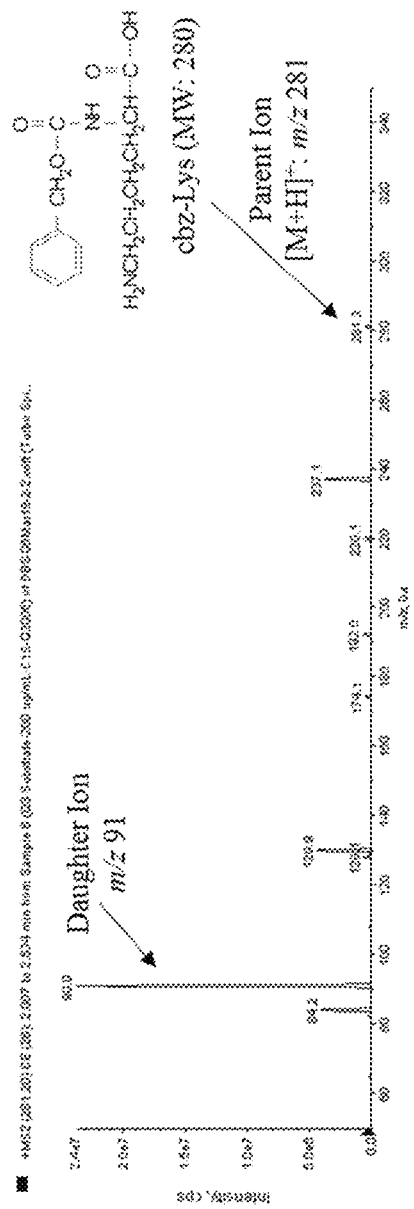
FIG. 2 is an exemplary ion chromatogram illustrating the fragmentation pattern of the cbz-Lys parent ion under collision-induced dissociation (CID). The most intense peak at m/z 91 was selected as the product ion for detection.

FIG. 2 shows the fragmentation pattern of the cbz-Lys precursor ion under collision-induced dissociation (CID). The most intense peak at m/z 91 was chosen as the product ion for the detection.

FIG. 3 displays the ion chromatograms of the cbz-Lys and internal standard (IS) derived from (1) neat buffer solution as a control; (2) enzyme reaction product of the DBS extracts from surrogate matrix composed of the mixture of red blood cell and BSA solution at optimized volume ratio; (3) enzyme reaction product of the DBS extracts from an authentic whole blood sample from a healthy individual. The cbz-Lys and IS show reproducible retention from different sources of samples. In addition, the cbz-Lys peak intensities from the neat solution and surrogate blood matrix are very similar, implying the residual fC1-INH in the surrogate blood matrix is minimal. On the other hand, the cbz-Lys intensity derived from the healthy blood sample where the fC1-INH is normal is significantly lower, suggesting the inhibition of the C1s enzymatic activity by the presence of fC1-INH. The figure demonstrates the feasibility to detect the cbz-Lys following the enzyme reaction of the DBS extract.

Figure 4:
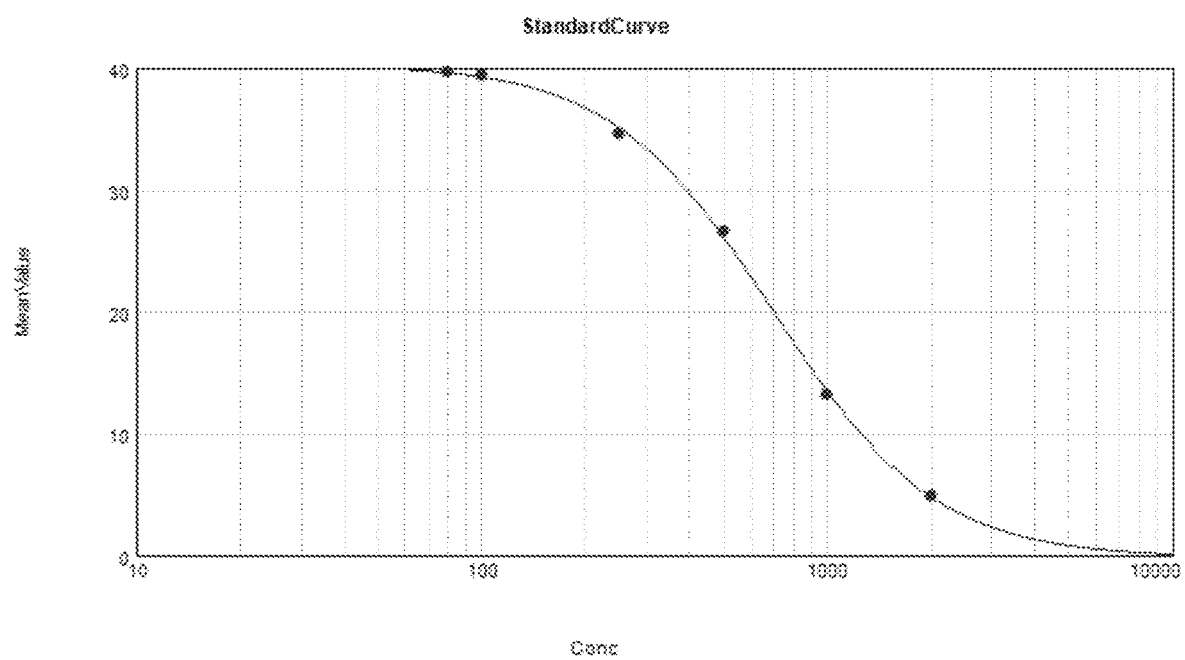
FIG. 4 is a calibration curve showing measurement of fC1-INH in a DBS.

A calibration curve for the measurement of fC1-INH in DBS is shown in FIG. 4.

In order to evaluate the inter-run reproducibility of the DBS-based LC-MS/MS fC1-INH assay, pooled blood sample from six individual subjects were collected and analyzed using the DBS-based LC-MS/MS fC1-INH assay on three different days. The results of the assay are shown in Table 1. The precision of the assay (% CV-10.3) is excellent.

TABLE 1

Inter-Run Reproducibility of DBS-Based LC-MS/MS fC1-INH assay Pooled Whole Blood (WB) was prepared from six lots of subjects

| Run Date/No. | Measured Conc. (mU/mL) | Ave. Conc. (mU/mL) | Intra SD | Intra CV (%) |
|---|---|---|---|---|
| 15 Nov. 2018 (Run #1) | 559 | 507 | 54.5 | 10.8 |
|  | 542 |  |  |  |
|  | 495 |  |  |  |
|  | 557 |  |  |  |
|  | 460 |  |  |  |
|  | 429 |  |  |  |
| 16 Nov. 2018 (Run #3) | 567 | 491 | 43.2 | 8.8 |
|  | 502 |  |  |  |
|  | 501 |  |  |  |
|  | 459 |  |  |  |
|  | 455 |  |  |  |
|  | 459 |  |  |  |
| 19 Nov. 2018 (Run #5) | 573 | 556 | 44.0 | 7.9 |
|  | 563 |  |  |  |
|  | 604 |  |  |  |
|  | 536 |  |  |  |
|  | 479 |  |  |  |
|  | 583 |  |  |  |
| Inter Ave. (mU/mL) |  | 518 |  |  |
| Inter SD |  |  | 53.1 |  |
| Inter CV (%) |  |  |  | 10.3 |

To evaluate the intra-day reproducibility of the DBS-based LC-MS/MS fC1-INH assay, C1-INH was spiked into the Red Blood Cell Matrix at different concentrations as quality controls (lower limit of quantitation (LLOQ), Low, Mid and High). The samples were then analyzed using DBS-based LC-MS/MS fC1-INH assay. The results are shown in Table 2. The level of fC1-INH obtained from the assay corresponds to the level of fC1-INH that was spiked into the samples, indicating the precision of this assay in measuring fC1-INH using DBS.

TABLE 2

Intra-Day Reproducibility of DBS-Based LC-MS/MS fC1-INH Assay

| | QC Samples | | Intra-day (n = 6) | | |
|---|---|---|---|---|---|
| Sample Name | Sample Matrix | Nominal Conc. (mU/mL) | Measured Conc. ± S.D. (mU/mL) | R.S.D. (%) | RE (%) |
| QC LLOQ | Red Blood Cell + BSA Matrix | 100 | 97.9 ± 10.4 | 10.6 | −2.2 |
| QC Low |  | 150 | 136 ± 10.4 | 7.7 | −9.3 |
| QC Mid |  | 750 | 745 ± 22.0 | 3.0 | −0.7 |
| QC High |  | 1130 | 1064 ± 69.4 | 6.5 | −5.8 |

Example 2: Use of the DBS-Based LC-MS/MS fC1-INH Assay

Described herein is the development and validation of a novel assay capable of measuring fC1-INH activity in DBS for the diagnosis of HAE patients. The assay was validated following the regulatory guidelines and industry's best practices. DBS samples from HAE patients showed significantly lower fC1-INH activity, allowing the differentiation of HAE patients from healthy subjects.

Experimental Procedures (i) Materials $N^\alpha$-Carbobenzyloxy-Lys-ThioBenzyl ester hydrochloride (Z-Lys-SBzl·HCl, C1s Substrate) and $N^\varepsilon$-Benzyloxycarbonyl-L-lysine-2,6,6-d3 ($N^\varepsilon$—CBZ-L-lysine-d3, Internal Standard) were purchased from BACHEM (Torrance, Calif., USA) and CDN Isotopes (Quebec, Canada), respectively. Recombinant human complement component C1s (C1s) was purchased from R&D System (Minneapolis, Minn., USA). Recombinant C1-INH (CINRYZE®) was obtained in house. Bovine serum albumin (BSA) was obtained from Americanbio (Natick, Mass., USA). Sodium dodecyl sulfate (SDS) solution (10%) was product of Sigma (St. Louis, Mo., USA). The 500 µL 96-well plate (Eppendorf Protein LoBind) was purchased from Eppendorf (Hamburg, Germany). The 3 mm puncher and Whatman #903 protein saver cards were purchased from GE Health Care Life Science (Little Chalfont, Buckinghamshire, UK). Desiccants (1 g) and biohazard bags were obtained from VWR (Radnor, Pa., US). All other chemicals used in the study were the highest grade and were used without further purification.

(ii) Preparation of Solutions

C1s working solution (0.5 µg/mL) was freshly prepared by 734-fold dilution of C1s stock solution (367 µg/mL) with 0.5% BSA solution prepared in PBS buffer. Substrate stock solution was prepared by dissolving Z-Lys-SBzl·HCl in DMSO to a final concentration of 10 mM. Internal standard (IS) stock solution (2.5 mM) was prepared by dissolving $N^\varepsilon$—CBZ-L-lysine-d3 in 5 mM $Na_2CO_3$ in methanol/water (50/50) solution. Substrate, C1s, and IS stock solutions were stored at −80° C. prior to use. Substrate-IS cocktail containing 0.83 mM of Z-Lys-SBzl·HCl and 33.3 µM of $N^\varepsilon$—CBZ-L-lysine-d3 was prepared freshly in PBS buffer. The SDS solution (0.1%) was prepared by 100-fold dilution of 10% SDS with methanol/water (80/20, V/V) solution.

(iii) Preparation of DBS Samples

Whole blood from 24 previously diagnosed HAE patients were provided with patient's written informed consent. The blood was drawn into Vacutainer EDTA tubes and stored at 4° C. Within 24 hours of collection, the tubes were inverted several times to resuspend blood cells, and a 60 µL aliquot was spotted onto the filter paper spot. Normal human whole blood from 103 healthy subjects as purchased from BIOIVT (Westbury, N.Y., USA). Blood spots were dried for at least 3 hours at room temperature and were stored in sealed biohazard bags at −20° C. with one desiccant in each bag.

(iv) Preparation of C1-INH-Free Blood as Surrogate Matrix

To obtain surrogate matrix depleted of fC1-INH for the preparation of a calibration curve and quality control (QC), six different lots of human whole blood samples (three males and three females, 10 mL each) were prepared as described in Example 1. Briefly, the whole blood was centrifuged at room temperature for 10 min at 1200×g. The supernatant plasma was removed, and red blood cells were washed with 5 mL of PBS solution to remove residual plasma and fC1-INH. The red blood cells were isolated again by centrifugation at room temperature at 1200×g for 10 min. The resulting fC1-INH-free red blood cells were pooled. The surrogate blood matrix was prepared by mixing equal volumes of pooled red blood cells and 4.3% BSA prepared in PBS buffer.

(v) Preparation of Calibration Standards and QC Samples in DBS

Calibration standards (calibrators) were prepared by spiking different concentrations of fC1-INH (CINRYZE®) into the surrogate matrix. Nominal fC1-INH concentrations were 100, 200, 300, 500, 1000, and 1500 mU/mL, respectively. The quality control (QC) samples were prepared in either surrogate matrix or pooled human whole blood. The lower limit of quantification (LLOQ) QC (100 mU/mL) and Low QC (150 mU/mL) were prepared in surrogate matrix. All other QCs were prepared in pooled whole blood by taking into consideration endogenous C1-INH levels (EL): Low-Mid QC (EL), Mid QC (EL+200 mU/mL), Mid-High QC (EL+500 mU/mL), and High QC (EL+800 mU/mL). Preparation of calibrators and QCs in DBS followed the same procedure described above.

(vi) Sample Extraction and Enzymatic Reaction

Samples were extracted and enzymatic reactions were performed as described in Example 1. Briefly, a DBS disc was cut using a 3 mm puncher and was transferred to a 500 µL 96-well plate. The proteins in the disc were extracted by incubating in 100 µL of 0.5% BSA in PBS in a Thermomixer incubator with vortexing at 1250 rpm at a temperature of 37° C. for 3 hours. The plate was centrifuged at 4000 rpm for 3 min, and 20 µL of the extracts were then transferred to another 96-well plate containing 50 µL of C1s working solution. This was followed by incubation at 800 rpm and 37° C. for 1.5 hours. Subsequently, 105 µL of the substrate-internal standard (substrate-IS) cocktail was added to the above solution, followed by incubation at 800 rpm at room temperature in the dark for 40 min. The reaction was terminated by transferring 50 µL of the solution to 450 µL of 0.1% SDS in MeOH/Water (80/20, v/v). The resulting samples were further diluted 200-fold with MeOH/Water (80/20, v/v) prior to LC-MS/MS analysis.

(vii) LC-MS/MS Analysis

The reaction samples were analyzed by LC-MS/MS as described in Example 1. Briefly, separation of the substrate (Z-Lys-SBzl·HCl), the analyte ($N^\alpha$-Benzyloxycarbonyl-L-lysine, cbz-Lys), and IS ($N^\varepsilon$—CBZ-L-lysine-d3) was achieved on a Waters Acquity UPLC system, using a reversed-phase column (Waters Xbridge Protein BEH C4, 3.5 µm, 2.1×50 mm) with column temperature maintained at 30° C. The mobile phase A was 0.1% formic acid in water, and the mobile phase B was acetonitrile. The flow rate was 0.3 mL/min and the mobile phase gradient was as follows (time, % B): 0 min, 4%; 0.5 min, 4%; 3.5 min, 12%; 3.6 min, 70%; 4.6 min, 70%; 4.7 min, 4%; 5.5 min, 4%. The autosampler was set at 4° C., and 3.0 µL of sample was injected using Partial-loop LC injection mode. The analyte and IS were quantified on an AB Sciex QTrap 6500 mass spectrometer operated in the Selected Reaction Monitoring (SRM) mode using positive ions. The optimal MS parameters were as follows: Curtain Gas, 20; Collision Gas, medium; IonSpray Voltage, 4000; Temperature, 550; Ion Source Gas 1, 50; Ion Gas Source 2, 50; Declustering Potential, 120; Entrance Potential, 10.0; Collision Energy, 26.0; Collision Cell Exit Potential, 12.0. The analyte and IS were monitored using SRM ion pairs of m/z 281.2 to m/z 91.0 and m/z 284.2 to m/z 91.0, respectively.

(viii) Fit-for-Purpose Assay Validation

The fit-for-purpose assay validation followed industry's best practice for biomarkers and for DBS-based diagnostic assays (1-6). The method was validated for calibration curve, accuracy, precision, matrix effects, hematocrit, extraction, location of sampling, and stabilities under various conditions.

Accuracy (relative error or % RE) and precision (% RSD) were evaluated by analyzing six replicates of QC samples in both surrogate and authentic matrices at each concentration level each day for three days. Intra- and inter-day mean accuracy and precision were sequentially calculated. Analyte carry-over was examined by injecting a blank solution after running the upper limit of quantification (ULOQ) calibrator.

The impact of hematocrit levels on the assay performance was evaluated using whole blood from four healthy subjects. Briefly, plasma was separated from red blood cells by centrifugation at 1200×g for 10 min. Then, different volumes of plasma and red blood cells were mixed to achieve hematocrit levels of 25%, 45%, 60%, and 75%, respectively. DBS samples derived from 45% hematocrit was used as a reference for normalization of C1-INH activity at other hematocrit levels.

Figure 9:
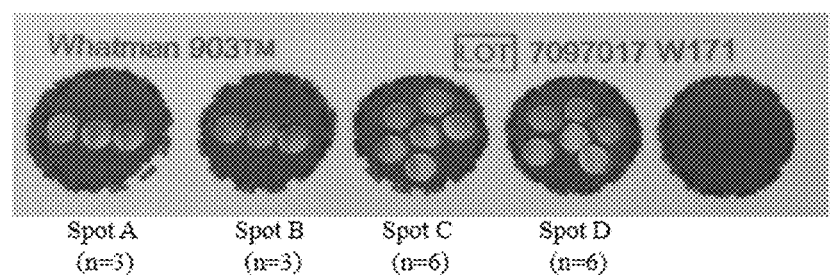
FIG. 9 is photograph showing DBS samples (Spots A-D) with punches (N=3 or =6) taken from different locations for analysis.

The effects of punch location on the DBS spot and variation of the DBS spots were assessed by using Low and Mid-High QC samples from 3-6 punch locations on a spot and from a total of four different DBS spots (FIG. 9, Table 3). The Low QC was prepared in surrogated matrix and Mid-High QC was prepared in pooled whole bloods.

$$y = D + \frac{A - D}{1 + \left(\frac{x}{C}\right)^2} \quad \text{(Equation 1)}$$

where y is the peak area ratio; x is sample concentration; A, B, C and D are curve fitting parameters. In addition, the mean, accuracy (% RE), standard deviation and relative standard deviation (% RSD) were calculated using Excel.

Results

Overall Strategy

Figure 5:
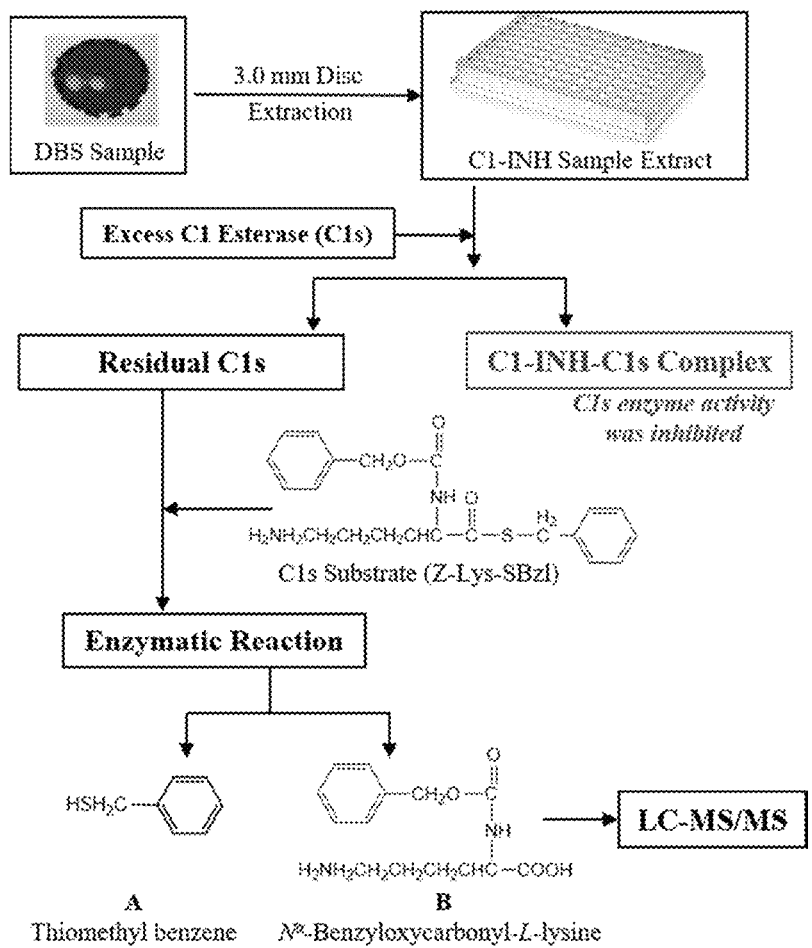
FIG. 5 is a schematic diagram illustrating an exemplary dried blood spot (DBS)-based fC1-INH liquid chromatography-tandem mass spectrometry (LC-MS/MS) assay for measuring a C1s product ($N^{\alpha}$-Benzyloxycarbonyl-L-lysine; cbz-Lys).

An LC-MS/MS assay was developed as illustrated in FIG. 5 to measure an enzyme reaction product, cbz-Lys, in samples derived from dried-blood spots. The assay consists of the following steps: (1) extraction of C1-INH from the DBS cards; (2) binding of C1-INH with excess C1s; (3) reaction of unbound C1s with its substrate; and (4) LC-MS/MS analysis of the enzyme reaction product cbz-Lys. Assay conditions were optimized during pre-validation runs, such as relative concentrations of C1s and its substrate, binding time and temperature between C1s and fC1-INH, enzymatic reaction time and temperature between C1s and its substrate, as well as LC-MS/MS conditions.

Calibration Matrix and Calibration Curve

A C1-INH-depleted blood matrix was prepared from pooled human whole blood in order to measure C1-INH

TABLE 3

Summary of the DBS homogeneity test

| | QC Samples | |
|---|---|---|
| | Low QC is surrogate matrix | Mid-High QC in authentic matrix |
| Nominal Conc. (mU/mL) | 150 | 1020 |
| Matrix | Red blood cells refurnished with BSA | Pooled Whole Blood |
| Total Replicates, N | 18 | 18 |
| Measured Conc. ± S.D. (mU/mL) | 143 ± 13.1 | 915 ± 75.0 |
| R.S.D (%) | 9.2 | 8.2 |
| RE (%) | −4.6 | −10.3 |

Extraction efficiency was evaluated by comparing the results of the pre-spiked samples with post-spiked samples using QCs prepared in surrogate matrix at 100, 600 and 1000 mU/mL. Pre-spiked samples were prepared by spiking C1-INH into surrogate matrix prior to preparing DBS cards. Post-spiked samples, on the other hand, were prepared by spiking the same concentration of C1-INH (3.3 µL, corresponding to wet blood volume in a 3.0 mm punch) into the DBS extracts derived from the blank surrogate matrix.

The whole blood stability of C1-INH activity was tested using equal volume of pooled whole blood from six healthy subjects (3 males and 3 females). The samples were stored at 4° C. for up to 7 days before adding to Whatman #903 protein saver cards. Similarly, DBS samples prepared from pooled whole bloods were stored at 45° C. for 3 days and at room temperature for 134 days to evaluate the stability under shipping and storage conditions, respectively.

(ix) Data Analysis

The data analysis was performed as described in Example 1. Briefly, peak area ratios of the analyte over internal standard were determined by AB Sciex Analyst (1.6.3). A 4-parameter logistic calibration curve was constructed with peak area ratios and the concentration of spiked C1-INH using SoftMax Pro 7.0. Sample concentration was calculated based on following equation:

activity in HAE patients where its activity is lower than the normal control. C1-INH is a circulating protein and will stay with plasma supernatant after centrifugation to spin down red blood cells. The red blood cells were subsequently replenished with BSA solution to mimic the plasma protein concentration in authentic whole blood. 4.3% of the BSA (43 mg/mL) mixed with the same volume of red blood cells gave rise to a similar viscosity as the authentic whole blood, as demonstrated by the same spot size in the filter paper. As shown in FIGS. 6A and 6B, complete depletion of C1-INH was confirmed by the same analyte signals from the surrogate matrix and blank control, implying the absence of fC1-INH activity in the surrogate matrix. In contrast, there is a C1-INH dependent signal attenuation in pooled healthy blood (FIG. 6C) and the pooled healthy blood spiked with 500 mU/mL of C1-INH (FIG. 6D).

Figure 7:
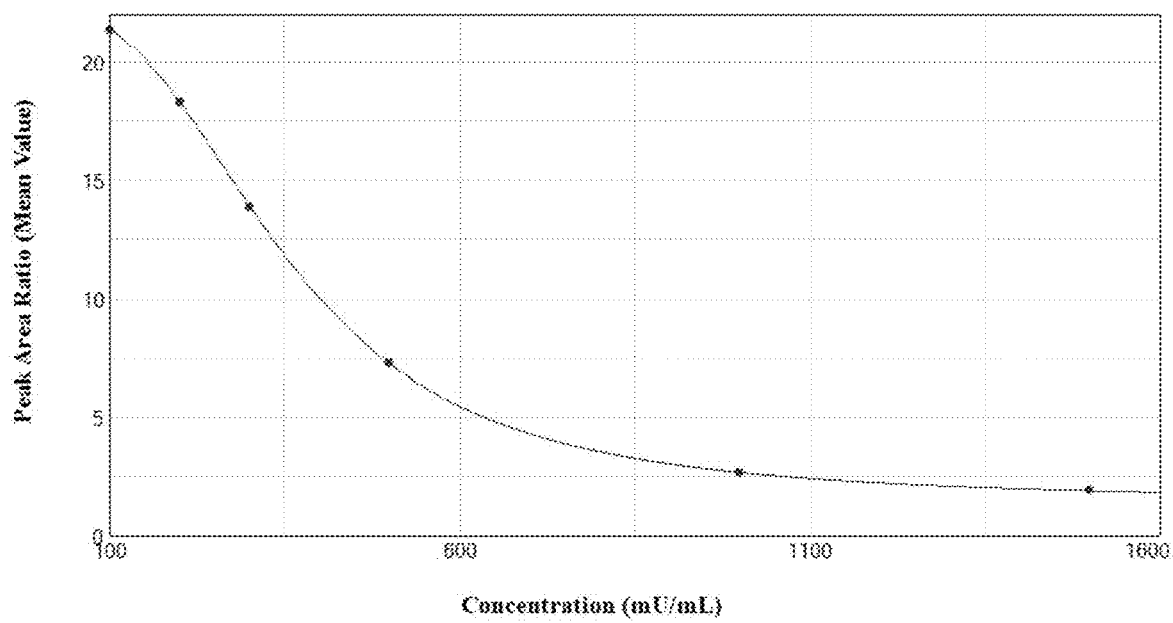
FIG. 7 is a representative calibration curve showing measurement of fC1-INH in a DBS.

FIG. 7 displays a typical calibration curve by plotting the analyte signals vs. six different C1-INH concentrations (mU/mL) spiked into the surrogate matrix, using a four-parameter logistic curve fit. The curve shows a workable range from 100 to 1500 mU/mL. Assay validation results demonstrated that the six points calibration curves met the preset criteria: (1) relative error (% RE) should be ≤20% for at least half of the calibrators at each concentration level, except for LLOQ and ULOQ calibrators which are ≤25%; (2) ≥75% of the total number of calibrators must be included in the calibration curve; (3) No more than two consecutive validation runs should fail. Of the 13 out of 14 passed analytical runs, mean inter-run accuracy of all calibrators ranged from −1.4% to 5.9% (Table 4).

tion of 100 mU/mL and 150 mU/mL, respectively. The pooled whole blood was used as a Low-Mid QC, whereas Mid, Mid-High, and High QC samples were prepared by spiking fC1-INH into the pooled whole blood. Their nominal concentrations were the sum of the mean endogenous

TABLE 4

Summary of Calibration Results

| Standards | Std 1 (100 mU/mL) | | Std 2 (200 mU/mL) | | Std 3 (300 mU/mL) | | Std 4 (500 mU/mL) | | Std 5 (1000 mU/mL) | | Std 6 (1500 mU/mL) | |
|---|---|---|---|---|---|---|---|---|---|---|---|---|
| | Measured Conc. (mU/mL) | Accuracy Bias (%) | Measured Conc. (mU/mL) | Accuracy Bias (%) | Measured Conc. (mU/mL) | Accuracy Bias (%) | Measured Conc. (mU/mL) | Accuracy Bias (%) | Measured Conc. (mU/mL) | Accuracy Bias (%) | Measured Conc. (mU/mL) | Accuracy Bias (%) |
| Run#1 | 98.4 | −1.6 | 184 | −8.0 | 284 | −5.3 | 446 | −10.8 | 887 | −11.3 | 1490 | −0.7 |
| | 104 | 4.0 | 213 | 6.5 | 321 | 7.0 | 567 | 13.4 | 1180 | 18.0 | 1850 | 23.3 |
| Run#2 | 88 | −12.0 | 197 | −1.5 | 283 | −5.7 | 495 | −1.0 | 1050 | 5.0 | 1250 | −16.7 |
| | 108 | 8.0 | 207 | 3.5 | 312 | 4.0 | 514 | 2.8 | 1050 | 5.0 | 1450 | −3.3 |
| Run#3 | 101 | 1.0 | 203 | 1.5 | 297 | −1.0 | 498 | −0.4 | 1050 | 5.0 | 1340 | −10.7 |
| | 101 | 1.0 | 193 | −3.5 | 309 | 3.0 | 492 | −1.6 | 998 | −0.2 | 1680 | 12.0 |
| Run#4 | 92.8 | −7.2 | 201 | 0.5 | 301 | 0.3 | 489 | −2.2 | 1070 | 7.0 | 1370 | −8.7 |
| | 110 | 10.0 | 192 | −4.0 | 310 | 3.3 | 492 | −1.6 | 990 | −1.0 | 1800 | 20.0 |
| Run#5 | 99.7 | −0.3 | 184 | −8.0 | 297 | −1.0 | 497 | −0.6 | 996 | −0.4 | 1310 | −12.7 |
| | 99.7 | −0.3 | 217 | 8.5 | 302 | 0.7 | 503 | 0.6 | 1100 | 10.0 | 1460 | −2.7 |
| Run#6 | 64.8 | −35.2 | 191 | −4.5 | 284 | −5.3 | 460 | −8.0 | 915 | −8.5 | n/a | n/a |
| | 124 | 24.0 | 207 | 3.5 | 322 | 7.3 | 536 | 7.2 | 1210 | 21.0 | n/a | n/a |
| Run#7 | 97.8 | −2.2 | 199 | −0.5 | 287 | −4.3 | 479 | −4.2 | 989 | −1.1 | 1300 | −13.3 |
| | 103 | 3.0 | 199 | −0.5 | 316 | 5.3 | 517 | 3.4 | 1060 | 6.0 | 1730 | 15.3 |
| Run#8 | 100 | 0.0 | 207 | 3.5 | 325 | 8.3 | 509 | 1.8 | 1120 | 12.0 | 1450 | −3.3 |
| | 100 | 0.0 | 187 | −6.5 | 291 | −3.0 | 461 | −7.8 | 1040 | 4.0 | 1360 | −9.3 |
| Run#9 | 123 | 23.0 | 206 | 3.0 | 300 | 0.0 | 463 | −7.4 | 1140 | 14.0 | 1350 | −10.0 |
| | 73.7 | −26.3 | 188 | −6.0 | 315 | 5.0 | 507 | 1.4 | 1070 | 7.0 | 1370 | −8.7 |
| Run#10 | 96.5 | −3.5 | 182 | −9.0 | 294 | −2.0 | 450 | −10.0 | 1050 | 5.0 | 1310 | −12.7 |
| | 103 | 3.0 | 214 | 7.0 | 323 | 7.7 | 517 | 3.4 | 1140 | 14.0 | 1480 | −1.3 |
| Run#11 | 105 | 5.0 | 202 | 1.0 | 324 | 8.0 | 477 | −4.6 | 1100 | 10.0 | 1370 | −8.7 |
| | 94.7 | −5.3 | 194 | −3.0 | 293 | −2.3 | 485 | −3.0 | 1100 | 10.0 | 1390 | −7.3 |
| Run#12 | 108 | 8.0 | 200 | 0.0 | 299 | −0.3 | 475 | −5.0 | 963 | −3.7 | 1370 | −8.7 |
| | 91.6 | −8.4 | 200 | 0.0 | 302 | 0.7 | 526 | 5.2 | 1070 | 7.0 | 1610 | 7.3 |
| Run#13 | 88.2 | −11.8 | 195 | −2.5 | 302 | 0.7 | 479 | −4.2 | 1060 | 6.0 | 1390 | −7.3 |
| | 111 | 11.0 | 207 | 3.5 | 302 | 0.7 | 493 | −1.4 | 1120 | 12.0 | 1400 | −6.7 |
| Run#14 | 94.6 | −5.4 | 195 | −2.5 | 292 | −2.7 | 473 | −5.4 | 1050 | 5.0 | 1390 | −7.3 |
| | 106 | 6.0 | 202 | 1.0 | 319 | 6.3 | 504 | 0.8 | 1080 | 8.0 | 1430 | −4.7 |
| Mean Conc. (mU/mL) | 99.6 | | 199 | | 304 | | 493 | | 1059 | | 1450 | |
| Mean Bias (%) | −0.4 | | −0.6 | | 1.3 | | −1.4 | | 5.9 | | −3.3 | |
| SD | 12.1 | | 9.2 | | 13.1 | | 26.7 | | 72.4 | | 157 | |
| CV (%) | 12.2 | | 4.6 | | 4.3 | | 5.4 | | 6.8 | | 10.8 | |

Assay Precision and Accuracy

Assay precision and accuracy were assessed using QC samples prepared in both surrogate matrix and authentic whole blood. The LLOQ QC and Low QC were prepared by spiking fC1-INH into surrogate matrix to a final concentration of 100 mU/mL and 150 mU/mL, respectively. The pooled whole blood was used as a Low-Mid QC, whereas Mid, Mid-High, and High QC samples were prepared by spiking fC1-INH into the pooled whole blood. Their nominal concentrations were the sum of the mean endogenous C1-INH concentration (518 mU/mL, n=18) and concentration of spiked fC1-INH. As shown in Table 5, the intra-day precision and accuracy ranged from 4.4% to 11.6%, and −11.1% to −2.1%, and inter-day precision and accuracy were 8.1% to 13.1%, and −10.3% to 0.9%, respectively.

TABLE 5

Summary of intra-day and inter-day precision and accuracy

| QC Samples | | | Intra-day (n = 6) | | | Inter-day (n =18) | | |
|---|---|---|---|---|---|---|---|---|
| QC Name | Sample Matrix | Nominal Conc. (mU/mL) | Measured Conc. ± S.D. (mU/mL) | R.S.D (%) | RE (%) | Measured Conc. ± S.D. (mU/mL) | R.S.D (%) | RE (%) |
| LLOQ QC | Surrogate Matrix | 100 | 97.9 ± 10.4 | 10.6 | −2.2 | 99.1 ± 9.40 | 9.5 | 0.9 |
| Low QC | | 150 | 134 ± 5.3 | 4.0 | −10.8 | 143 ± 13.1 | 9.2 | −4.6 |
| Low-Mid QC (EL) | Pooled Whole | 518 | 507 ± 54.5 | 10.8 | −2.1 | 518 ± 53.1 | 10.3 | N/A |

TABLE 5-continued

Summary of intra-day and inter-day precision and accuracy

| QC Name | Sample Matrix | Nominal Conc. (mU/mL) | Intra-day (n = 6) | | | Inter-day (n =18) | | |
|---|---|---|---|---|---|---|---|---|
| | | | Measured Conc. ± S.D. (mU/mL) | R.S.D (%) | RE (%) | Measured Conc. ± S.D. (mU/mL) | R.S.D (%) | RE (%) |
| Mid QC (EL + 200 mU/mL) | Blood | 718 | 639 ± 73.9 | 11.6 | −11.1 | 651 ± 52.7 | 8.1 | −9.4 |
| Mid-High QC (EL + 500 mU/mL) | | 1020 | 991 ± 44.1 | 4.4 | −2.8 | 915 ± 75.0 | 8.2 | −10.3 |
| High QC (EL + 800 mU/mL) | | 1320 | 1187 ± 118 | 10.0 | −10.1 | 1250 ± 163 | 13.1 | −5.5 |

Effect of Hematocrit Levels

It is well documented that hematocrit level of the whole blood affects the blood dilution in filter paper and thus DBS spot size, resulting in assay bias (1-3, 6, 7). As the hematocrit levels increase, the spot area of DBS samples decreases. Depending on the gender and age, hematocrit level in whole blood ranges from 28% to 67% (7). Effect of hematocrit on assay performance was investigated at four hematocrit levels, 25%, 45%, 60% and 75%, where 45% hematocrit level was used as a control. The fC1-INH activities showed a linear correlation with hematocrit levels in the dried blood spots (Table 6). Hematocrit levels of between 30%-60% should have minimal effect on fC1-INH activity measurement (RE<20%).

Punch Location of C1-INH Activity

Another concern in DBS based assay is the effect of punch location on the analyte measurement (1, 6, 8). To examine the effect of punch position on a DBS card on C1-INH activity, a total of 18 replicated samples from central and peripheral punches were collected from four spots of the same subject and analyzed for Low QC and Mid-High QC samples. Both precision and accuracy were within 15%, implying punch positions did not impact C1-INH activity measurement (Table 4).

Extraction Efficiency

Extraction efficiency of C1-INH was evaluated using QCs prepared in surrogate matrix. The mean extraction efficiencies were 48.8%, 65.9% and 58.2% respectively at QC concentrations of 100, 600 and 1000 mU/mL (Table 7). A calibration curve was used in each run during sample testing, variation in the extraction efficiency would not affect the assay accuracy.

TABLE 6

Effect of hematocrit levels on the fC1-INH activity measured in DBS

| Sample ID | Hematocrit Level (%) | Measured Conc. ± S.D. (mU/mL, n = 4) | Theoretical Conc (mU/mL) | R.S.D. (%) | RE % |
|---|---|---|---|---|---|
| HMN13491 | 25 | 572 ± 76.1 | 851 | 13.3 | −32.8 |
| | 45 | 624 ± 32.3 | 624 | 5.2 | 0 |
| | 60 | 463 ± 81.8 | 454 | 17.7 | 2.00 |
| | 75 | 406 ± 16.6 | 284 | 4.1 | 43.0 |
| HMN13492 | 25 | 793 ± 74.4 | 1055 | 9.4 | −24.8 |
| | 45 | 774 ± 95.3 | 774 | 12.3 | 0 |
| | 60 | 643 ± 42.5 | 563 | 6.6 | 14.2 |
| | 75 | 502 ± 21.1 | 352 | 4.2 | 42.6 |
| HMN13493 | 25 | 835 ± 139 | 1189 | 16.7 | −29.8 |
| | 45 | 872 ± 123 | 872 | 14.1 | 0 |
| | 60 | 582 ± 50.9 | 634 | 8.7 | −8.20 |
| | 75 | 478 ± 27.0 | 396 | 5.6 | 20.7 |
| HMN13494 | 25 | 766 ± 83.6 | 949 | 10.9 | −19.3 |
| | 45 | 696 ± 66.1 | 695 | 9.5 | 0 |
| | 60 | 587 ± 48.0 | 506 | 8.2 | 16.0 |
| | 75 | 497 ± 34.2 | 316 | 6.9 | 57.3 |

TABLE 7

Extraction Efficiency of C1-INH in DBS samples

| Conc (mU/mL) | Extraction Efficiency ± S.D. (%, n = 4) | R.S.D. (%) |
|---|---|---|
| 100 | 48.8 ± 4.92 | 10.1 |
| 600 | 65.9 ± 3.93 | 6.0 |
| 1000 | 58.2 ± 3.45 | 5.9 | fC1-INH Stability in Whole Blood and DBS

The stability of fC1-INH was evaluated in whole blood. A previous report demonstrated that the fC1-INH is stable for up to three days at room temperature in both patient and healthy subjects (9). fC1-INH activity in pooled healthy blood had minimal change after storage at 4° C. for seven days (Table 8). To test the fC1-INH stability in DBS, QC controls were placed in airtight bags with desiccant packs at room temperature and 45° C. C1-INH activity was measured in different punches from each card and showed minimal loss (<15%) after 3 days of storage at 45° C. and 134 days when stored at room temperature (Table 8). These results demonstrated that fC1-INH can be shipped and stored at ambient temperatures in DBS without losing activity.

TABLE 8

Stability of fC1-INH activity in whole blood and DBS stored at different temperatures

| Matrix | Storage Temp. (° C.) | Days of storage | Measured Conc. ± S.D. (mU/mL) | R.S.D. (%) | RE (%) |
|---|---|---|---|---|---|
| Whole blood | 4° C. | 0 | 489 ± 54.2 (n = 4) | 11.1 | N/A |
| | | 5 | 497 ± 64.0 (n = 4) | 12.9 | 1.6 |
| | | 7 | 473 ± 33.8 (n = 4) | 7.2 | −3.3 |
| DBS | Room temp | 0 | 512 ± 56.2 (n = 18) | 11 | N/A |
| | | 134 | 441 ± 53.9 (n = 6) | 12.2 | −13.8 |
| | Room temp | 0 | 407 ± 13.6 (n = 6) | 3.3 | N/A |
| | 45° C. | 3 | 383 ± 36.8 (n = 6) | 9.6 | −5.8 |

The processed samples were re-injected after placed in an autosampler at 4° C. for two days to assess the re-injection stability. The results showed that the precision and accuracy met the pre-defined acceptance criteria (Table 9). In addition, analyte carry-over was not detectable (data not shown).

TABLE 9

Summary of re-injection stability test

| | QC Samples | | Intra-day (n = 6) | | |
|---|---|---|---|---|---|
| Sample Name | Sample Matrix | Nominal Conc. (mU/mL) | Measured Conc. ± S.D. (mU/mL) | R.S.D. (%) | RE (%) |
| Low QC | Red Cell Matrix | 150 | 145 ± 13.9 | 9.6 | −3.1 |
| Low-Mid QC (Pooled Whole Blood, EL) | Pooled Whole Blood | 518 | 488 ± 44.3 | 9.1 | −5.7 |
| Mid QC (EL + 200 mU/mL) | | 718 | 845 ± 52.8 | 8.2 | −10.2 |
| Mid-High QC (EL + 500 mU/mL) | | 1020 | 867 ± 48.5 | 5.6 | −15.0 |
| High QC (EL + 800 mU/mL) | | 1320 | 1200 ± 74.4 | 6.2 | −8.8 |

Analysis of DBS Samples from Healthy and HAE Subjects

Figure 8:
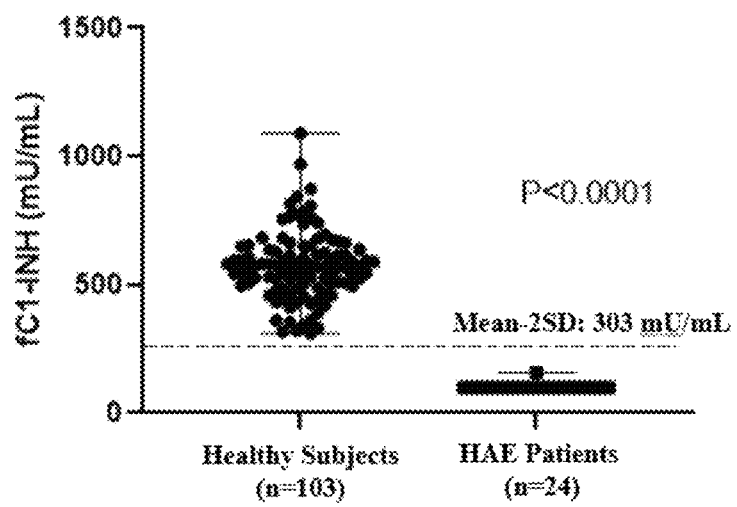
FIG. 8 is a plot showing fC1-INH levels in samples from healthy subjects (n=103) and HAE patients (n=24). mU/mL is milliUnits of functional C1-INH levels per milliliter.

Using the validated assay, fC1-INH activity was measured in DBS samples collected from 103 healthy subjects and 24 HAE patients (9 males and 15 females) and results are presented in FIG. 8. For the healthy subject group, the fC1-INH activity ranged from 311 to 1090 mU/mL, with mean activity and standard deviation (SD) at 573 and 135 mU/mL, respectively. Nevertheless, all tested HAE subjects had C1-INH activities below LLOQ (100 mU/mL), except for one subject whose C1-INH was 158 mU/mL. A cut-off value (Mean−2×SD) of 303 mU/mL was established, which was capable of completely differentiating healthy from HAE subjects.

Discussion

C1-INH functions to regulate a wide range of inhibitory biological activities that include complement, contact, coagulation and fibrinolytic system (10-12). As a key inhibitor of three enzymes (Factor XIIa, Factor XIIf, and plasma kallikrein) in the kallikrein-kinin cascade, normal fC1-INH levels prevent the overproduction of bradykinin, a proinflammatory mediator that induces HAE attack. Deficient fC1-INH activity results in the recurrent activation of contact system, generating excess plasma kallikrein (pKal), an active proteolytic enzyme, which in turn cleaves the high-molecular-weight kininogen (HMWK) to release bradykinin (13-15). Currently, more than 450 mutations have been identified throughout the C1-INH SERPING1 gene and many are associated with fC1-INH deficiency in HAE patients (16).

Although there are different types of HAE, all are characterized by deficient C1-INH function. Typically, fC1-INH levels in HAE patients is between 5-30% of normal values and attenuated C1-INH activity is used as the most important laboratory parameter for HAE diagnosis (9). Conventional assays for fC1-INH activity indirectly measure fC1-INH activity by means of the reaction between C1s and its artificial substrate, Z-Lys-SBzl·HCl, to produce cbz-Lys and thiomethyl benzene. Thiomethyl benzene is measured by chromogenic assay, after derivatization with 5,5'-dithiobis-(2-nitrobenzoic acid) (DTNB) (9). Presence of endogenous or spike-in C1-INH would inhibit the enzyme reaction, therefore, formation of the reaction products is inversely proportional to C1-INH activity. While the conventional assay is powerful to differentiate healthy and HAE subjects in plasma or serum samples, its usage in DBS was limited due to the assay interferences by the red blood cells in whole blood. The LC-MS/MS assay possesses unique advantages over the conventional chromogenic assay. First, the chromogenic assay is based on two steps of reactions, whereas the LC-MS/MS assay measures a direct product of the C1s reaction, therefore assay variation can be lower. Secondly, use of internal standard (IS) in the assay also aids to correct the analytical variation during sample preparation and analysis. Third, the calibration curve and QCs prepared in the C1-INH-free surrogate matrix were included in each run to further enhance accuracy and reproducibility of the assay. Considering the broad range of the C1-INH activity in healthy subjects, the limited C1-INH activity shift in HAE patients (5-30% of the normal activity), and the narrow range of the enzyme kinetic reaction, minimizing assay variation can be a key factor to accurate measurement of C1-INH activity.

In an enzyme activity assay, a calibration curve of the analyte is usually prepared in neat buffer solution rather than authentic matrix, and assay performance is monitored by the QC samples. While this approach is simple, it cannot be readily applied to C1-INH activity measurement because the enzyme reaction proceeds so rapidly that a slight shift in reaction conditions would affect the analytical results and thus the accurate diagnosis of the patients. The concept of "surrogate matrix" that has been widely utilized in the preparation of calibrators and QCs in biomarker assays as authentic matrix contains endogenous analyte was adopted in these studies (15). The surrogate matrix should be depleted of the analyte but close to the authentic matrix with regard to digestion efficiency, ionization effects and extraction yield. Use of surrogate matrix derived from whole blood for the preparation of calibration curve and QCs is critical to accurately assess the enzyme reaction in patient samples, where the C1-INH activity is low. With this approach, an assay range between 100 to 1500 mU/mL was attained. Furthermore, excellent accuracy and precision were achieved from QC samples prepared in both surrogate matrix and authentic whole blood, demonstrating parallelism of the two matrices under the assay conditions.

The LC-MS/MS assay described here showed a mean intra- and inter-day variability of less than 15% and negligible carry-over between samples. In addition, C1-INH activity measurement was independent of the punch location within the DBS, which has not been the case for some other analytes in DBS (1). However, the assay accuracy may be affected by the hematocrit levels, and caution should be taken to interpret the test results from samples with hematocrit levels of less than 30% or more than 60%.

It is important to have stable analyte levels in DBS during sample transportation and storage. C1-INH in whole blood was stable for 7 days at 4° C. In DBS, it was stable for up to 3 days when stored at 45° C. and 134 days when stored at room temperature. This is sufficient for the entire duration of sample collection, shipment to central laboratories, and laboratory testing and re-testing, even in developing countries.

The C1-INH activities measured in 103 healthy subjects showed a normal distribution with a mean activity of 573 mU/mL and a standard deviation of 135 mU/mL. Among the 24 HAE patients, 23 showed <100 mU/mL C1-INH activity, and the HAE sample with the highest C1-INH activity, 158 mU/mL, corresponded to 27.6% of the mean normal activity. The data supports an unambiguous distinction between samples from healthy individuals and corresponding samples from patients with HAE.

In conclusion, described herein is a robust assay for fC1-INH activity in DBS samples. The assay offers superior reproducibility and accuracy for diagnosis of HAE patients. Simple sample collection and prolonged shipment and storage stability expand the availability of the diagnostic tests, particularly in places where there is limited or no access to fully equipped clinical laboratories. The assay shows the great potential to fundamentally change the algorithm of HAE diagnostics worldwide.

REFERENCES

1. Holub M, Tuschl K, Ratschmann R, Strnadova K A, Muhl A, Heinze G, et al. Influence of hematocrit and localisation of punch in dried blood spots on levels of amino acids and acylcarnitines measured by tandem mass spectrometry. Clin Chim Acta 2006; 373:27-31.
2. De Jesus V R, Zhang X K, Keutzer J, Bodamer O A, Muhl A, Orsini J J, et al. Development and evaluation of quality control dried blood spot materials in newborn screening for lysosomal storage disorders. Clin Chem 2009; 55:158-64.
3. de Vries R, Barfield M, van de Merbel N, Schmid B, Siethoff C, Ortiz J, et al. The effect of hematocrit on bioanalysis of dbs: Results from the ebf dbs-microsampling consortium. Bioanalysis 2013; 5:2147-60.
4. Lee J W, Devanarayan V, Barrett Y C, Weiner R, Allinson J, Fountain S, et al. Fit-for-purpose method development and validation for successful biomarker measurement. Pharm Res 2006; 23:312-28.
5. McDade T W. Development and validation of assay protocols for use with dried blood spot samples. Am J Hum Biol 2014; 26:1-9.
6. Timmerman P, White S, Globig S, Ludtke S, Brunet L, Smeraglia J. Ebf recommendation on the validation of bioanalytical methods for dried blood spots. Bioanalysis 2011; 3:1567-75.
7. Denniff P, Spooner N. The effect of hematocrit on assay bias when using DBS samples for the quantitative bioanalysis of drugs. Bioanalysis 2010; 2:1385-95.
8. Cobb Z, de Vries R, Spooner N, Williams S, Staelens L, Doig M, et al. In-depth study of homogeneity in DBS using two different techniques: Results from the EBF DBS-microsampling consortium. Bioanalysis 2013; 5:2161-9.
9. Wagenaar-Bos I G, Drouet C, Aygoren-Pursun E, Bork K, Bucher C, Bygum A, et al. Functional C1-inhibitor diagnostics in hereditary angioedema: Assay evaluation and recommendations. J Immunol Methods 2008; 338:14-20.
10. Bork K, Davis-Lorton M. Overview of hereditary angioedema caused by C1-inhibitor deficiency: Assessment and clinical management. Eur Ann Allergy Clin Immunol 2013; 45:7-16.
11. Csuka D, Veszeli N, Varga L, Prohaszka Z, Farkas H. The role of the complement system in hereditary angioedema. Mol Immunol 2017; 89:59-68.
12. Ratnoff O D, Pensky J, Ogston D, Naff G B. The inhibition of plasmin, plasma kallikrein, plasma permeability factor, and the C'1r subcomponent of the first component of complement by serum C1 esterase inhibitor. J Exp Med 1969; 129:315-31.
13. Nzeako U C, Frigas E, Tremaine W J. Hereditary angioedema: A broad review for clinicians. Arch Intern Med 2001; 161:2417-29.
14. Bernstein J A, Moellman J. Emerging concepts in the diagnosis and treatment of patients with undifferentiated angioedema. Int J Emerg Med 2012; 5:39.
15. Zhang G, Sexton D J, Faucette R R, Qiu Y, Wu J. 2d-lc-ms/ms to measure cleaved high-molecular-weight kininogen in human plasma as a biomarker for C1-INH-HAE. Bioanalysis 2017; 9:1477-91.
16. Johnsrud I, Kulseth M A, Rodningen O K, Landro L, Helsing P, Waage Nielsen E, Heimdal K. A nationwide study of norwegian patients with hereditary angioedema with C1 inhibitor deficiency identified six novel mutations in SERPING1. PLoS One 2015; 10:e0131637.
17. Maurer M, Magerl M, Ansotegui I, Aygoren-Pursun E, Betschel S, Bork K, et al. The international wao/eaaci guideline for the management of hereditary angioedema—the 2017 revision and update. Allergy 2018; 73:1575-96.
18. Li H H, Busse P, Lumry W R, Frazer-Abel A, Levy H, Steele T, et al. Comparison of chromogenic and ELISA functional C1 inhibitor tests in diagnosing hereditary angioedema. J Allergy Clin Immunol Pract 2015; 3:200-5.
19. Ganz N, Singrasa M, Nicolas L, Gutierrez M, Dingemanse J, Dobelin W, Glinski M. Development and validation of a fully automated online human dried blood spot analysis of bosentan and its metabolites using the sample card and prep dbs system. J Chromatogr B Analyt Technol Biomed Life Sci 2012; 885-886:50-60.
20. Holub M, Tuschl K, Ratschmann R, Strnadova K A, Muhl A, Heinze G, et al. Influence of hematocrit and localisation of punch in dried blood spots on levels of amino acids and acylcarnitines measured by tandem mass spectrometry. Clin Chim Acta 2006; 373:27-31.
21. Matern D, Oglesbee D, Tortorelli S. Newborn screening for lysosomal storage disorders and other neuronopathic conditions. Dev Disabil Res Rev 2013; 17:247-53.
22. Mokhtariye A, Hagh-Nazari L, Varasteh A R, Keyfi F. Diagnostic methods for lysosomal storage disease. Rep Biochem Mol Biol 2019; 7:119-28.
23. Zhang X K, Elbin C S, Chuang W L, Cooper S K, Marashio C A, Beauregard C, Keutzer J M. Multiplex enzyme assay screening of dried blood spots for lysosomal storage disorders by using tandem mass spectrometry. Clin Chem 2008; 54:1725-8.
24. Olivova P, van der Veen K, Cullen E, Rose M, Zhang X K, Sims K B, et al. Effect of sample collection on alpha-galactosidase an enzyme activity measurements in dried blood spots on filter paper. Clin Chim Acta 2009; 403:159-62.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method for determining a level of functional C1-esterase inhibitor (fC1-INH) in a sample, the method comprising:
   (i) spotting a blood sample from a subject on a support member;
   (ii) drying the blood sample on the support member to form a dried blood spot;
   (iii) extracting proteins from the dried blood spot from (ii); and
   (iv) measuring the level of fC1-INH in the extracted proteins in (iii), if present;
   wherein measuring the level of fC1-INH comprises:
      (a) incubating the extracted proteins with a complement component 1s (C1s) and a C1s substrate, to produce a C1s substrate product;
      (b) measuring the level of the C1s substrate product produced in step (a); and
      (c) determining the level of fC1-INH in the dried blood spot based on the level of the C1s substrate product measured in step (b).

2. The method of claim 1, wherein step (iv)(a) is performed by incubating the extracted proteins with the C1s and the C1s substrate to produce a reaction mixture.

3. The method of claim 1, wherein the measuring step of step (iv)(b) is performed by liquid chromatography-mass spectrometry.

4. The method of claim 1, wherein the C1s substrate is $N^{\alpha}$-Carbobenzyloxy-Lys-ThioBenzyl ester and the C1s substrate product is $N^{\alpha}$-Benzyloxycarbonyl-L-lysine (cbz-Lys).

5. The method of claim 1, wherein the extracting of (iii) is performed by incubating the dried blood spot with a bovine serum albumin (BSA)/phosphate buffered saline (PBS) buffer for at least 3 hours.

6. The method of claim 1, wherein the support member is a filter paper.

7. The method of claim 1, wherein the drying of step (ii) is performed for at least 3 hours at room temperature.

8. The method of claim 1, further comprising obtaining the blood sample from the subject.

9. The method of claim 1, wherein the blood sample is a whole blood sample.

10. The method of claim 1, wherein subject is a human subject.

11. The method of claim 10, wherein the subject has, is suspected of having, or is at risk for having hereditary angioedema (HAE).

12. The method claim 11, wherein the HAE is Type I HAE or Type II HAE.

13. The method of claim 1, further comprising determining whether the subject has a C1-INH-deficiency-mediated disorder, wherein a reduced level of fC1-INH product as compared with a control indicates that the subject has the C1-INH-deficiency-mediated disorder.

14. The method of claim 13, further comprising identifying a suitable treatment for the subject having the C1-INH-deficiency-mediated disorder based on the level of fC1-INH.

15. The method of claim 1, further comprising identifying the subject as a candidate for treatment of a C1-INH deficiency-mediated disorder based on the level of fC1-INH determined in step (iv)(c) compared to a control level, wherein the control level is the level of fC1-INH in a sample obtained from a healthy subject.

16. The method of claim 1, further comprising administering a therapeutic agent to the subject, if the subject is identified as being at risk for or having a C1-INH deficiency-mediated disorder based on the level of fC1-INH determined in step (c) compared to a control level, wherein the control level is the level of fC1-INH in a sample obtained from a healthy subject.

17. The method of claim 16, wherein the therapeutic agent is a plasma kallikrein (pKal) inhibitor, a bradykinin B2 receptor antagonist, or a C1 esterase inhibitor.

18. The method of claim 16, wherein the therapeutic agent is ecallantide, lanadelumab, icatibant, or a human plasma-derived C1 esterase inhibitor.

19. The method of claim 13, wherein the C1-INH deficiency-mediated disorder is HAE.

20. The method of claim 19, wherein the HAE is Type I HAE or Type II HAE.

* * * * *